US012678214B2

(12) United States Patent
Sherman

(10) Patent No.: US 12,678,214 B2
(45) Date of Patent: Jul. 14, 2026

(54) POWER UNIT FOR DELIVERING COHERENT SINE BURST IRREVERSIBLE ELECTROPORATION ENERGY TO A BIOLOGICAL TISSUE

(71) Applicant: ARGÁ MEDTECH SA, Chardonne (CH)

(72) Inventor: Marshall Sherman, Cardiff by the Sea, CA (US)

(73) Assignee: Argá Medtech SA, Epalinges (CH)

( * ) Notice: Subject to any disclaimer, the term of this patent is extended or adjusted under 35 U.S.C. 154(b) by 319 days.

(21) Appl. No.: 18/338,135

(22) Filed: Jun. 20, 2023

(65) Prior Publication Data

US 2024/0180606 A1 Jun. 6, 2024

Related U.S. Application Data

(63) Continuation-in-part of application No. PCT/EP2021/087138, filed on Dec. 21, 2021, which
(Continued)

(51) Int. Cl.
*A61B 18/12* (2006.01)
*A61B 18/00* (2006.01)

(52) U.S. Cl.
CPC .............................. *A61B 18/1206* (2013.01); *A61B 2018/00613* (2013.01); *A61B 2018/00732* (2013.01);
(Continued)

(58) Field of Classification Search
CPC ...... A61B 18/1206; A61B 2018/00613; A61B 2018/00732; A61B 2018/00761; A61B 2018/124; A61B 2018/128
(Continued)

(56) References Cited

U.S. PATENT DOCUMENTS

2003/0120310 A1 6/2003 Mulhauser
2007/0083239 A1 4/2007 Demarais et al.
(Continued)

FOREIGN PATENT DOCUMENTS

| CN | 111248994 A | 6/2020 |
| CN | 111265295 A | 6/2020 |
| CN | 112055568 A | 12/2020 |
| WO | 2019133608 A1 | 7/2019 |

OTHER PUBLICATIONS

International Search Report and Written Opinion issued on May 6, 2022, in counterpart International Patent Application No. PCT/EP2021/087138 (12 pages).
(Continued)

*Primary Examiner* — Beverly M Flanagan
(74) *Attorney, Agent, or Firm* — Bookoff McAndrews, PLLC

(57) ABSTRACT

A power unit for supplying electric energy to at least one electrode of an electronic apparatus for delivering Coherent Sine Burst Irreversible Electroporation energy, including at least one power module to generate an electric signal (S) to energize one or more respective electrodes, the power module comprising a selecting block configured to receive at least one square wave input signal and continuously change the electric energy level associated with said electric signal (S) based on the at least one square wave input signal in order to provide a combined signal at an output of the selecting block, wherein the combined signal comprises a square wave waveform; and a filtering and electrical isolation block configured to convert the combined signal into a sine wave signal and to filter the sine wave signal to generate the electric signal (S), wherein the conversion and filtering are electrically isolated from one another.

20 Claims, 9 Drawing Sheets

Related U.S. Application Data is a continuation of application No. PCT/US2020/
066444, filed on Dec. 21, 2020, application No.
18/338,135, filed on Jun. 20, 2023 is a continuation of
application No. PCT/US2020/066444, filed on Dec.
21, 2020.

(52) U.S. Cl.
CPC .............. *A61B 2018/00761* (2013.01); *A61B 2018/124* (2013.01)

(58) Field of Classification Search
USPC .......................................................... 606/34
See application file for complete search history.

(56) References Cited

U.S. PATENT DOCUMENTS

2010/0023004 A1      1/2010   Francischelli et al.
2021/0177503 A1*    6/2021   Altmann ................ A61B 18/00

OTHER PUBLICATIONS

International Search Report and Written Opinion issued on Sep. 30, 2021, in counterpart International Patent Application No. PCT/US2020/0664444 (13 pages).

* cited by examiner

POWER UNIT FOR DELIVERING COHERENT SINE BURST IRREVERSIBLE ELECTROPORATION ENERGY TO A BIOLOGICAL TISSUE

CROSS-REFERENCE TO RELATED APPLICATION(S)

This application is a continuation-in-part application under 35 U.S.C. § 111(a) of pending International Application No. PCT/EP2021/087138, filed on Dec. 21, 2021, and a continuation-in-part application under 35 U.S.C. § 111(a) of pending International Application No. PCT/US2020/066444, filed on Dec. 21, 2020.

DESCRIPTION

Field of the Invention

The present invention generally relates to a power unit for supplying electric energy to a plurality of electrodes of an electronic apparatus.

Particularly, the present invention relates to a power unit for supplying electric energy to a plurality of electrodes of an electronic apparatus for delivering Coherent Sine Burst Irreversible Electroporation energy, wherein the power unit is configured to generate an electric signal to energize each of the electrodes.

Background Art

Tissue ablation is used in numerous medical procedures to treat a patient. Ablation can be performed to remove or denature undesired tissue such as diseased cardiac cells. The ablation can be performed by passing energy, such as electrical energy, through one or more electrodes and causing tissue death where the electrodes are in contact. Ablation procedures can be performed on patients with any cardiac arrhythmia such as atrial fibrillation (AF) by ablating tissue in the heart.

Radiofrequency ablation (RFA) is a medical procedure in which part of the electrical conduction system of the heart, tumor or other dysfunctional tissue is ablated using the heat generated from medium frequency alternating current, e.g. in the range of 350-500 KHz.

Particularly, in this procedure an energy delivery device, such as a probe with or without a needle, is inserted into a target tissue to cause destruction of a target region of the cardiac tissue through the application of thermal energy. In fact, electrically induced thermal ablation such as RFA can be used to effectively and continuously locally ablate a tissue site as the energy delivery device is placed on the tissue surface. Although RFA can effectively ablate volumes of target tissue, there are limitations to this technique. One often cited problem using this procedure during cardiac ablation involves heat sink, a process whereby one aspect can include blood flow whereas the heat generated on the ablation element will be removed/dissipated by the cooler blood flows over the element. This heat dissipation effect can change both the shape and maximum volume of the tissue being ablated.

More recently, to ablate cardiac or organ tissue, Pulsed Electric Fields (PEF) have been used as an alternative to the above-mentioned RFA. Pulsed Electric Fields (PEF) refer to application of intermittent, high-intensity electric fields for short periods of time (micro or nanoseconds), which results in cellular and tissue electroporation. Electroporation is a process whereby an applied electric field (i.e. PEF) results in the formation of pores in cell membranes. Pore formation leads to permeabilization, which can be reversible or irreversible, depending upon parameters of the applied PEF.

In reversible electroporation, cells remain viable, and underlies the basis of electrochemotherapy and gene electrotransfer. In contrast, with irreversible electroporation (IRE), cells and tissue are non-viable because of programmed cell death cascade activation.

IRE is a well-established treatment for solid tumors. However, IRE may also be useful in cardiology, particularly for cardiac ablation, given limitations of current thermal based approaches.

When used to ablate cardiac tissue, IRreversible Electroporation (IRE) involves the application of electrical pulses to targeted tissue in the range of microseconds to milliseconds that can lead to non-thermally produced defects in the cell membrane that are nanoscale in size. These defects can lead to a disruption of homeostasis of the cell membrane, thereby causing irreversible cell membrane permeabilization which induces cell necrosis, without raising the temperature of the tissue ablation zone.

Typical PEF parameters to cause IRE include 10-90 pulses, with a pulse length of microseconds or nanoseconds (usually 100 μs), at a frequency of 1-10 Hz, and with an electric field between 500 and 3000 V/cm. See reference Elad Maor et al "Pulsed electric fields for cardiac ablation and beyond: A state-of-the-art review", Heart Rhythm 2019; 16:1112-1120).

One challenge in designing PEF protocols is separating the effects electric fields can have on biological tissues. An electric field applied across tissue will induce heat by Joule's first law, which states power of heating is proportional to resistance and square of the current. To overcome this and to solely obtain electroporation damage, most PEF protocols use ultrashort pulses (microseconds) at low frequency (1-10 Hz). This balances heating with the cooling effect of physiological heat conduction and convection, preventing significant rises in temperature.

IRE performed with unipolar electrical pulses has the disadvantage of causing intense muscle contractions. Therefore, clinical applications of IRE require the administration of general anesthesia and neuroparalytic agents in order to eliminate the discomfort caused by muscle contractions seen during each pulse. However, receiving paralytic agents is undesirable for patients, and may deter them from seeking an electroporation based therapy.

Electronic systems are known in the art for delivering IRreversible Electroporation (IRE) energy to a biological tissue, wherein these electronic systems are configured to generate high-frequency, bipolar waveforms for mitigating muscle contractions during electroporation based therapies.

In particular, High-Frequency IRE (H-FIRE) is a technique for non-thermal tissue ablation that eliminates muscle contractions seen in IRE treatments performed with unipolar electric pulses. In fact, no visual or tactile evidence of muscle contraction was seen during H-FIRE at 250 kHz or 500 kHz. Therefore, H-FIRE can be performed clinically without the administration of paralytic agents.

H-FIRE can involve the application of square wave electrical signals. For this purpose, it is known, for example, to use square wave signals centered at 500 kHz.

However, rectangular waveforms comprise signal components having various frequencies and amplitudes that could create dangerous effects when IRE is used to specifically treat cardiac tissue. For example, a traditional IRE square wave signal has a 150 Hz component at a voltage of around 6V, which poses a significant risk of heart stimulation.

The issue with squarewave pulsed electric fields are the similarities to that of an ICD (Internal Cardiac Defibrillator): these types of devices cause significant heart tissue damage when discharged. Using squarewave pulsed electric field can cause heart tissue damage outside the desired zone. As such, sedation is required and square-wave delivery has to be synchronized with the R-wave of an ECG.

It is therefore still strongly felt the need of providing an IRreversible Electroporation (IRE) based treatment for a biological tissue, especially the heart tissue, which avoids cardiac muscle stimulation and does not require sedation of the patients. Further, it is desirable to provide a power generator which can generate signals appropriate for the application of electroporation while ensuring patient safety. It is also desirable to ensure that a power generator for the generation of such signals is able to do so using practically sized and rated electronic components.

SUMMARY OF THE INVENTION

In the present disclosure, we provide an electronic apparatus for delivering Irreversible Electroporation (IRE) energy, particularly Coherent Sine Burst IRE, to a biological tissue to be treated, particularly a cardiac tissue, having structural and functional features such as to meet the aforementioned needs and overcome the drawbacks mentioned above with reference to the electronic systems of the prior art used for the same purpose. This disclosure is helpful for understanding the disclosure as a whole.

Particularly, the present disclosure provides for a novel electronic apparatus 100 for delivering Coherent Sine Burst Irreversible Electroporation energy, or IRE, to a biological tissue 1 to be treated, particularly a cardiac tissue.

The electronic apparatus 100 comprises:
  a plurality of electrodes 3 positionable either on or near the biological tissue 1 to be treated; and
  a power generator 2 for supplying electric energy to each of the electrodes 3 of said plurality.

It is a purpose of this invention to provide the power generator 2 configured to generate an electric signal S to energize each of said electrodes 3.

In one or more embodiments, the electric signal S is formed by alternating over time a first electric signal S1 with a second electric signal S2; the first electric signal S1 is supplied to the electrodes 3 during a first time interval T1 and the second electric signal S2 is supplied to the electrodes during a second time interval T2 subsequent to the first time interval T1; said first electric signal S1 is a continuous bipolar signal comprising two or more basic sine waves SB in said first time interval T1, each basic sine wave consisting in one positive half-wave and one negative half-wave; said second electric signal S2 having an amplitude equal to zero in said second time interval T2.

Applicant has verified that the electric signal S, generated by alternating over time the first electric signal S1, comprising two or more basic sine waves, with the second electric signal S2, having amplitude equal to zero, does not generate cardiac muscle stimulation. Therefore, in a first aspect, patients do not have to be sedated. In a further aspect, the delivery of energy does not have to be synchronized with the hearts R-wave of an ECG.

In the present disclosure, we further provide a method for controlling the plurality of electrodes in the electronic apparatus for delivering Coherent Sine Burst Irreversible Electroporation energy, wherein the electronic apparatus comprises a plurality of electrodes 3 and a power generator 2. The method involves generating by the power generator 2 an electric signal S for supplying electric energy to each of the electrodes 3 of said plurality, said electric signal S being formed by alternating over time a first electric signal S1 with a second electric signal S2, said first electric signal S1 is a continuous bipolar signal comprising two or more basic sine waves SB in a first time interval T1, each basic sine wave consisting in one positive half-wave and one negative half-wave, said second electric signal S2 having an amplitude equal to zero in a second time interval T2 subsequent to the first time interval T1. The method further comprising supplying said first electric signal S1 to the electrodes 3 of said plurality during the first time interval T1; supplying said second electric signal (S2) to the electrodes (3) of said plurality during the second time interval (T2).

It is a further purpose of this invention to provide an electronic apparatus 100 for delivering Irreversible Electroporation energy, or IRE, to a biological tissue 1 to be treated. The electronic apparatus comprises one or more electrodes 3 positionable either on or near the biological tissue 1 to be treated and a power generator 2 for supplying electric energy to said one or more electrodes 3; said power generator 2 is configured to generate an electric signal S to energize said one or more electrodes 3.

The electric signal S may be formed by alternating over time a first electric signal S1 with a second electric signal S2; said first electric signal S1 is supplied to the one or more electrodes 3 during a first time interval T1 and said second electric signal S2 is supplied to the one or more electrodes during a second time interval T2 subsequent to the first time interval T1; said first electric signal S1 has a periodic waveform in the first time interval T1; said second electric signal S2 has an amplitude equal to zero in the second time interval T2.

It is a further purpose of this invention to provide a power generator 2 for delivering Coherent Sine Burst Irreversible Electroporation energy, or IRE, to a biological tissue 1 to be treated. The power generator may comprise a single control unit 200 and a power unit 201 for generating an electric signal S formed by alternating over time a first electric signal S1 with a second electric signal S2; the power unit 201 comprises a power module 202 which may be driven by the single control unit 200 to generate said first electric signal S1 during a first time interval T1 and to generate said second electric signal S2 during a second time interval T2 subsequent to the first time interval T1; the first electric signal S1 is a continuous bipolar signal comprising two or more basic sine waves SB in said first time interval T1, each basic sine wave consisting in one positive half-wave and one negative half-wave; the second electric signal S2 has an amplitude equal to zero in said second time interval T2.

According to alternative examples, a method for the ablation of a biological tissue 1 is provided. The method involves the step of using the electronic apparatus 100 for delivering Coherent Sine Burst Irreversible Electroporation energy, or IRE, according to the invention.

According to alternative examples, a method for the treatment of a pathology in a patient is provided. The method involves the step of performing the ablation of a biological tissue 1 of said patient by using the electronic apparatus 100 for delivering Coherent Sine Burst Irreversible Electroporation energy, or IRE, according to the invention.

According to alternative examples, a method for the ablation of a biological tissue 1 by delivering Irreversible Electroporation energy, or IRE, is provided. The method involves the step of applying to said biological tissue 1 an electric signal S comprising at least a sine wave signal.

According to a preferred embodiment, said electric signal S is formed by alternating over time a first electric signal S1 with a second electric signal S2; said first electric signal S1 is applied during a first time interval T1 and said second electric signal S2 is applied during a second time interval T2 subsequent to the first time interval T1; the first electric signal S1 is a continuous bipolar signal comprising two or more basic sine waves SB in said first time interval T1, each basic sine wave consisting in one positive half-wave and one negative half-wave; the second electric signal S2 having an amplitude equal to zero in said second time interval T2, thereby causing the ablation of said biological tissue 1.

According to a further preferred embodiment, said first electric signal S1 has a frequency in the range of 25-49 kHz or in the range of 40-60 KHz.

According to alternative examples, a method for the treatment of a pathology in a patient by delivering Irreversible Electroporation energy, or IRE, is provided. The method comprises the step of applying to a biological tissue 1 of said patient an electric signal S formed by alternating over time a first electric signal S1 with a second electric signal S2; said first electric signal S1 is applied during a first time interval T1 and said second electric signal S2 is applied during a second time interval T2 subsequent to the first time interval T1; the first electric signal S1 is a continuous bipolar signal comprising two or more basic sine waves SB in said first time interval T1, each basic sine wave consisting in one positive half-wave and one negative half-wave; the second electric signal S2 has an amplitude equal to zero in said second time interval T2, thereby causing the ablation of said biological tissue 1.

According to a preferred embodiment, the first electric signal S1 has a frequency in the range of 25-49 kHz or in the range of 40-60 KHz. Some advantageous embodiments are the subject of the dependent claims.

According to a first aspect of the present disclosure, we provide a power unit for supplying electric energy to at least one electrode of an electronic apparatus for delivering Coherent Sine Burst Irreversible Electroporation energy, the power unit including at least one power module configured to generate an electric signal (S) to energize one or more respective electrodes, the or each power module comprising: a selecting block configured to receive at least one square wave input signal wherein the selecting block is configured to continuously change the electric energy level associated with said electric signal (S) based on the at least one square wave input signal in order to provide a combined signal at an output of the selecting block, wherein the combined signal comprises a square wave waveform; a filtering and electrical isolation block configured to convert the combined signal into a sine wave signal and to filter the sine wave signal to generate the electric signal (S), wherein the conversion and filtering are electrically isolated from one another.

An aspect according to the first aspect may be particularly advantageous, as it provides at least electrical isolation between the selecting block and the electrical signal (S). This electrical isolation may provide for enhanced safety for patients who are connected to the electrodes by isolating electrical DC voltages. This provision of inherent safety functionality in the circuit obviates the need for additional safety circuitry.

In one or more embodiments, the selecting block may comprise an H-Bridge circuit.

The use of an H-bridge may provide a particularly efficient way of continuously changing the electric energy level associated with the electric signal (S).

In one or more embodiments, the selecting block may comprise a charging capacitor having a first node coupled between a power supply terminal couplable to a second power supply voltage source and a ground terminal couplable to ground and wherein the charging capacitor is configured to be selectively discharged via the H-Bridge circuit based on the at least one square wave input signal, and wherein the selective discharging of the charging capacitor is configured to provide the combined signal at the output of the selecting block.

Such embodiments may provide for particularly advantageous and efficient way of providing the combined signal at the output of the selecting block.

In one or more embodiments, the H-Bridge Circuit may comprise: a first inverter branch comprising a first power switching element and a second power switching element; a second inverter branch comprising a third power switching element and a fourth power switching element; said first power switching element and third power switching element are connected between the power supply terminal couplable to the second power supply voltage in direct current and, respectively, a first output terminal and a second output terminal of the H-Bridge circuit; said second power switching element and fourth power switching element are connected between said first output terminal and second output terminal of the H-Bridge circuit and a ground terminal couplable to ground.

Such embodiments may provide a particularly efficient H-Bridge design capable of managing high current loads, such as 120-200 Amp currents continuously.

In one or more embodiments, the power switching elements may be power MOSFETs. MOSFETs, such as silicon carbide MOSFETs may provide for particularly advantageous components for handling the required currents and voltages of the switching block.

In one or more embodiments, the gate terminals of each of the first power switching element, the second power switching element, the third power switching element and the fourth power switching element may be controlled in response to the at least one square wave input signal in order to provide for the continuous change in electric energy level associated with the electric signal (S).

Such embodiments may provide for particularly advantageous ways of controlling the switching of the H-Bridge circuit.

In one or more embodiments, the filtering and electrical isolation block may comprise at least one of: a first series resonance filter configured to generate the sine wave signal by converting the square wave combined signal at the output of the selecting block; a step up transformer configured to provide for the electrical isolation by being configured to amplify said sine wave signal to generate a further sine wave signal; and a second series resonance filter configured to provide for filtering of the further sine wave in order to generate the electric signal to be supplied to the electrodes.

The first series resonance filter may provide an efficient way to convert the combined signal to a sine wave signal. The step up transformer may provide for the advantageous electrical isolation between conversion and filtering of the signal in addition to being able to step the voltage up to a predetermined voltage level. For example, the step up transformer may be a 1:3 or a 1:4 transformer. The second series resonance filter may advantageously filter out low frequency signals which may otherwise risk harming a patient, such as by stimulating the heart, and filtering out high frequency signals.

In one or more embodiments, the first series resonance filter may comprise a bandpass filter configured to convert the combined signal into the sine wave signal at a predetermined frequency.

The bandpass filter may comprise one or more inductors and capacitors. The bandpass filter may be an efficient way to convert the square wave into a sine wave.

In one or more embodiments, the step up transformer may comprise a step-up transformer with a high frequency ferrite core.

In one or more embodiments, the second series resonance filter may comprises one or both of: an inductor choke, wherein the inductor choke is configured to provide for filtering of frequencies higher than the predetermined frequency; and at least one filter capacitor, wherein the filter capacitor is configured to provide for filtering of frequencies lower than the predetermined frequency.

The one or both of an inductor choke and a capacitor may provide for particularly efficient ways to provide for filtering at a predetermined frequency. This may avoid providing a virtual ground within the second series resonance filter. This in turn may help in ensuring that other systems that are coupled to the electrodes, such as mapping and ECG systems, are not interfered with by the power module.

In one or more embodiments, the filtering and isolation block may further comprise one or both of: a current measurement circuit configured to measure a current of the electric signal (S); and a voltage measurement circuit configured to measure a voltage of the electric signal (S).

Providing for one or both of direct measurements of the current and voltage measurements of the electric signal (S) in the filtering and isolation block may provide for a true measure of the current, voltage and/or power being applied to the electrodes which are applied to a patient. This may allow for improved determination of the signals being applied to a patient and, thereby, improved control of the signals applied to a patient.

In one or more embodiments, the power generator may further comprise a drive circuit configured to receive a first drive signal (PS1) and a second drive signal (PS2) wherein the drive circuit is configured to amplify the first and second drive signals in order to provide a first square wave input signal and a second square wave input signal to the selecting block.

While the switching block may be able to be controlled by at least one square wave, providing for two square waves may make it easier to achieve switching at a desired high rate while avoiding the need for particularly large or expensive components that can switch at the necessary speeds and voltages.

In one or more embodiments, the first drive signal and the second drive signal may be received from a single control unit.

A single control unit may be configurable to efficiently generate and provide two drive signals and to ensure that the two drive signals, in certain embodiments, are not providing a logic high signal contemporaneously. This may be achieved by providing the two drive signals 180 degrees out of phase with each other and may further be achieved by providing each signal with a duty cycle of less than 50% to ensure no overlap between the logic high periods of the signals.

In one or more embodiments, the drive circuit may be configured in an emitter-follower configuration.

An emitter-follower configuration may provide an advantageous amplifier arrangement which makes optimal use of the components of the driver circuit.

In one or more embodiments, the drive circuit may comprise a first amplifier circuit and a second amplifier circuit, wherein each of the first and second amplifier circuits are arranged in an Emitter-Follower configuration identical to each other and each amplifier circuit is connected between a power terminal couplable to a first direct current power supply voltage and a ground potential (GND) terminal for connecting to ground.

Providing one amplifier circuit for each drive signal may be a particularly efficient way to handle the amplification of the first and second drive signals.

In one or more embodiments, the power generator may comprise a transformer circuit interposed between the drive circuit block and the selecting block, wherein the transformer circuit is configured to provide for electrical isolation between the drive circuit and the selecting block.

The provision of a transformer circuit may provide yet further electrical isolation of the patient from the power source and the drive signals, thereby providing yet further inherent protection functionality into the circuit while also providing an efficient way to drive the H-Bridge circuit.

In one or more embodiments, the transformer circuit may comprise a primary winding having a first terminal coupled to a first output terminal of the drive circuit block and a second terminal coupled to a second output terminal of the drive circuit block and the transformer further comprising a first secondary winding, a second secondary winding, a third secondary winding and a fourth secondary winding.

Providing for the transformer circuit coupled to first and second outputs of the drive circuit, which correspond to the outputs of the amplifier circuits, may provide for a particularly efficient way to provide for the two input signals to the H-Bridge. It will be appreciated that, in this arrangement wherein a first output of the drive circuit is coupled to a first terminal of the transformer and the second output of the drive circuit is coupled to the second, opposing, terminal of the drive circuit, output signals of the transformer may be, relatively, viewed as a logic high (logic 1), logic null (logic 0) and a logic low (logic −1). It will further be appreciated that, as used herein, "logic high" (logic 1) may refer to a positive voltage signal, but does not necessarily have to refer to a positive voltage signal. Similarly, "logic null" (logic 0) does may, but does not necessarily refer to a zero voltage signal. Finally, "logic low" (logic −1) may but does not necessarily refer to a negative voltage signal. These nomenclatures are simply used to provide an easy relative reference that those voltages may have relative to each other.

In one or more embodiments, the first drive signal and the second drive signal may be provided to the drive circuit such that the first square wave input signal and the second square wave input signal are not provided to the transformer circuit contemporaneously.

Receiving drive signals configured to not be provided to the transformer contemporaneously may avoid providing conflicting voltages in the circuit which may result in damaged components.

In one or more embodiments, each of the first secondary winding, the second secondary winding, the third secondary winding and the fourth secondary winding are coupled to a respective one of the first power switching element, second power switching element, third power switching element and fourth power switching element of the H-Bridge circuit such that the first and second square wave input signals provide for control of the first, second, third and fourth power switching elements.

Driving the power switching elements of the H-Bridge using the two input signals provided by the transformer may provide for a particularly synergistic system which can handle the required voltages, currents and powers in the switching block, providing switching signals of high enough amplitude to switch the power switching elements that are rated for such conditions while also electrically isolating the switching block components from the drive signals in order to provide for protection of those components.

According to a second aspect of the present disclosure, we provide a method for supplying electric energy to at least one electrode of an electronic apparatus for delivering Coherent Sine Burst Irreversible Electroporation energy comprising: receiving at least one square wave input signal at a selecting block; continuously changing the electric energy level associated with said electric signal (S) based on the at least one square wave input signal in order to provide a combined signal comprising a square wave waveform; receiving the combined signal at an input of a filtering and electrical isolation block from the selecting block; converting the combined signal into a sine wave signal; filtering the sine wave signal to generate the electric signal (S), wherein the conversion and filtering are electrically isolated from one-another.

According to a third aspect of the present disclosure, we provide a method for supplying electric energy to at least one electrode of an electronic apparatus for delivering Coherent Sine Burst Irreversible Electroporation energy comprising, wherein the at least one electrode is positioned within a patient: receiving at least one square wave input signal at a selecting block; continuously changing the electric energy level associated with said electric signal (S) based on the at least one square wave input signal in order to provide a combined signal comprising a square wave waveform; receiving the combined signal at an input of a filtering and electrical isolation block from the selecting block; converting the combined signal into a sine wave signal; filtering the sine wave signal to generate the electric signal (S), wherein the conversion and filtering are electrically isolated from one-another.

According to a fourth aspect of the present disclosure, we provide an electronic apparatus for delivering Coherent Sine Burst Irreversible Electroporation energy comprising a power unit for supplying electric energy to at least one electrode, the power unit including at least one power module configured to generate an electric signal (S) to energize one or more respective electrodes, the or each power module comprising: a selecting block configured to receive at least one square wave input signal wherein the selecting block is configured to continuously change the electric energy level associated with said electric signal (S) based on the at least one square wave input signal in order to provide a combined signal at an output of the selecting block, wherein the combined signal comprises a square wave waveform; a filtering and electrical isolation block configured to convert the combined signal into a sine wave signal and to filter the sine wave signal to generate the electric signal (S), wherein the conversion and filtering are electrically isolated from one another.

DRAWINGS

Further features and advantages of the invention will become apparent from the description provided below of exemplary embodiment thereof, given by way of non-limiting example, with reference to the accompanying drawings, in which:

FIG. 1 shows schematically an electronic apparatus for delivering Coherent Sine Burst Irreversible Electroporation energy, or IRE, to a biological tissue according to the present invention, wherein the electronic apparatus comprises a plurality of electrodes positionable either on or near the biological tissue to be treated, and a power generator for supplying electric energy to each of the electrodes;

Figure 1:
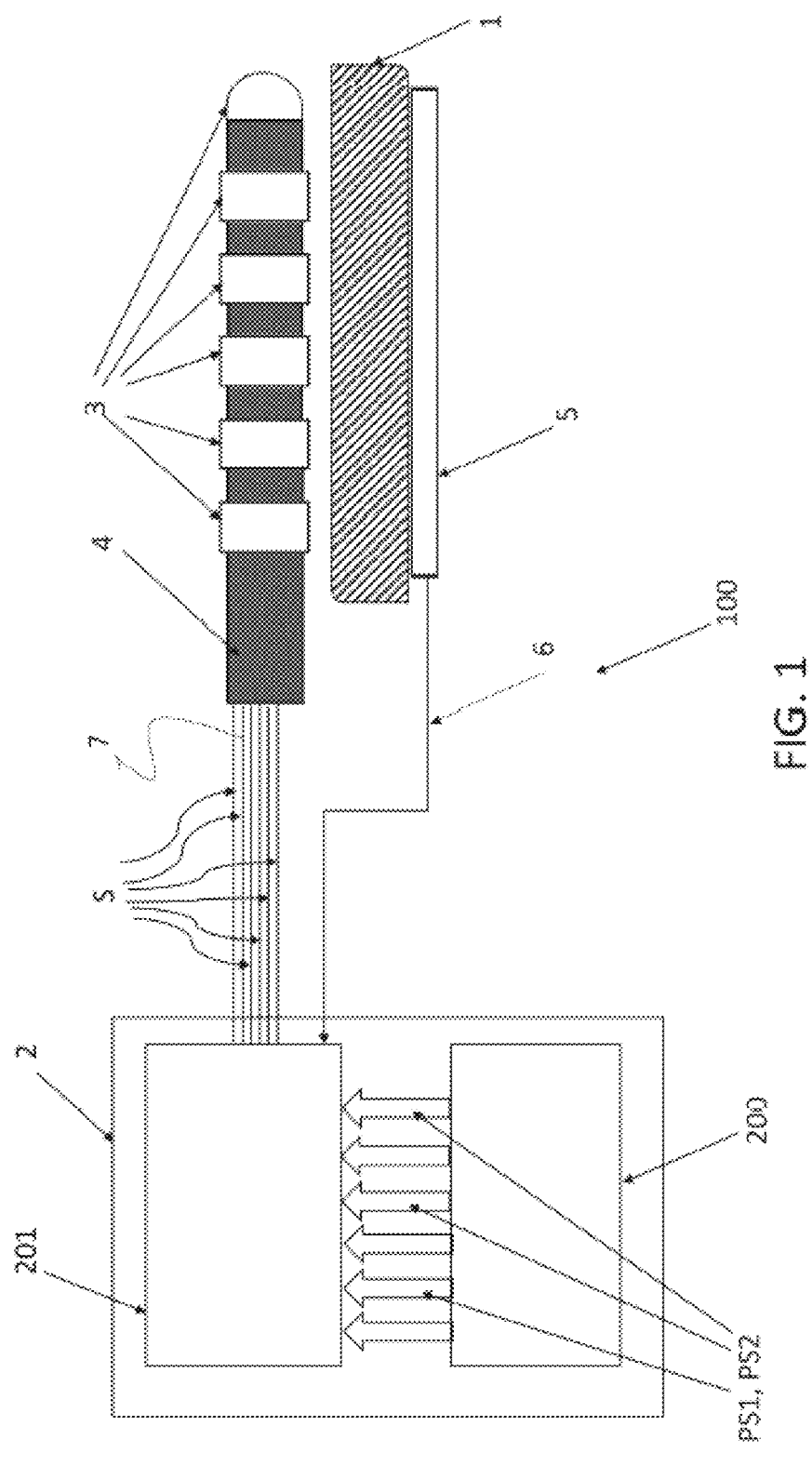
Figures 9, 10A, 10B:
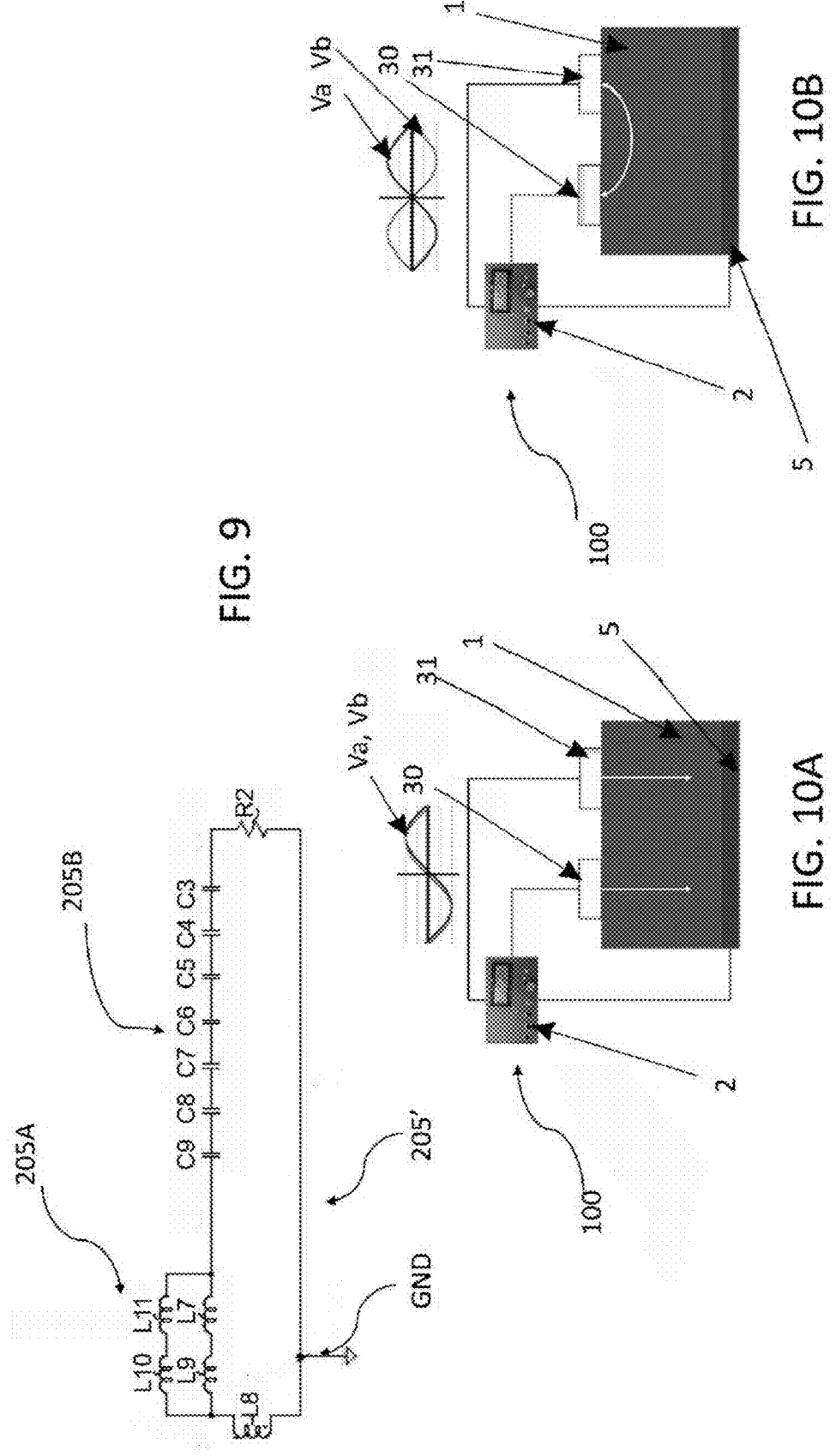
Figure 11:
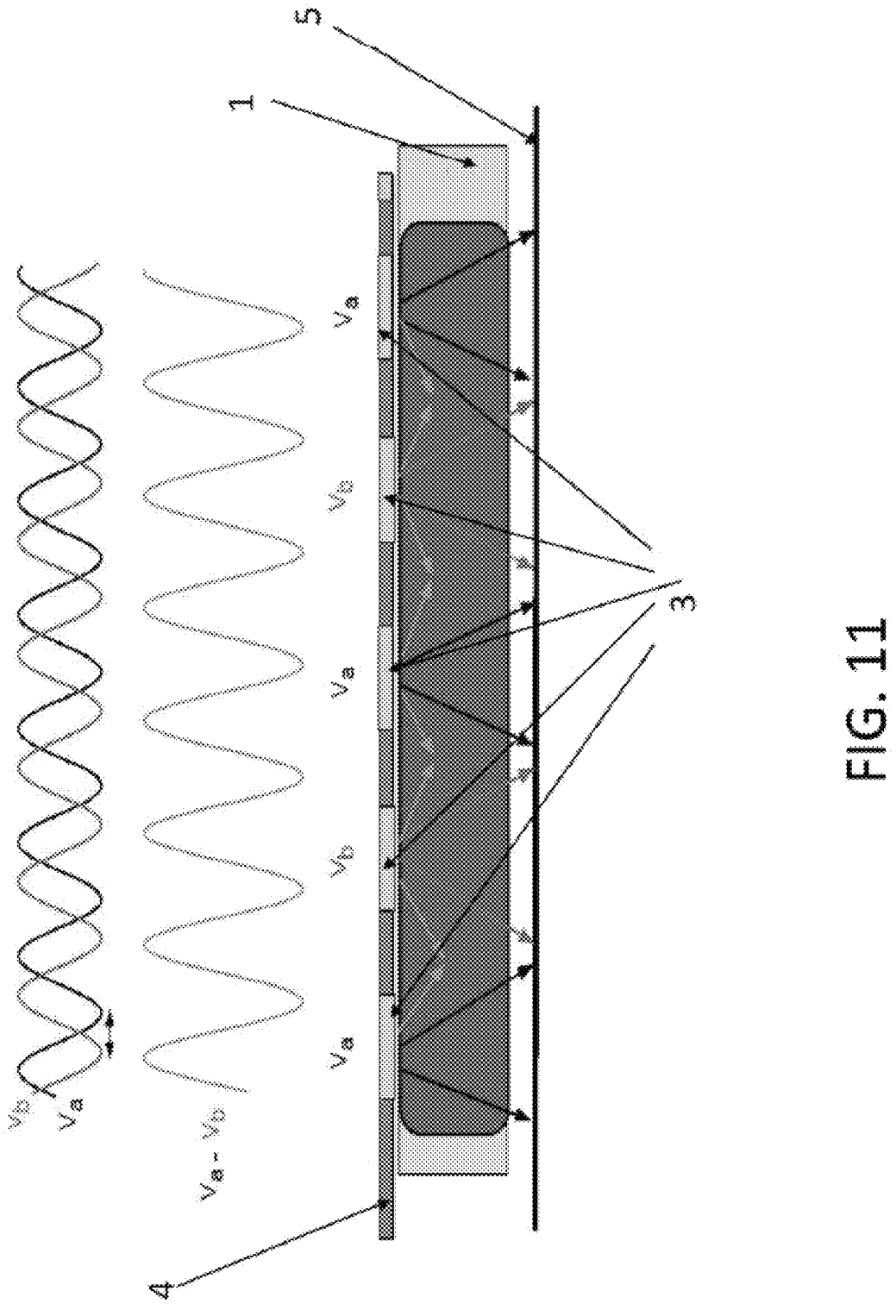

FIGS. 10A and 10B show schematically an electronic apparatus for delivering Coherent Sine Burst Irreversible Electroporation energy, or IRE, to a biological tissue according to the present invention, wherein the electronic apparatus comprises a first and a second electrodes positionable either on or near the biological tissue to be treated, and a power generator, this power generator being configured to supply both electrodes, respectively, with sine-waves electrical signals "in phase" or with sine-waves electrical signals "out of phase";

FIG. 11 shows schematically a plurality of electrodes electrically supplied by the power generator of apparatus of FIG. 1, wherein said electrodes are operatively associated to a catheter and positionable either on or near a myocardial tissue to be treated, and are configured to deliver combined bi-polar and uni-polar voltages or alternating uni-polar and bi-polar voltage fields.

Figure 2:
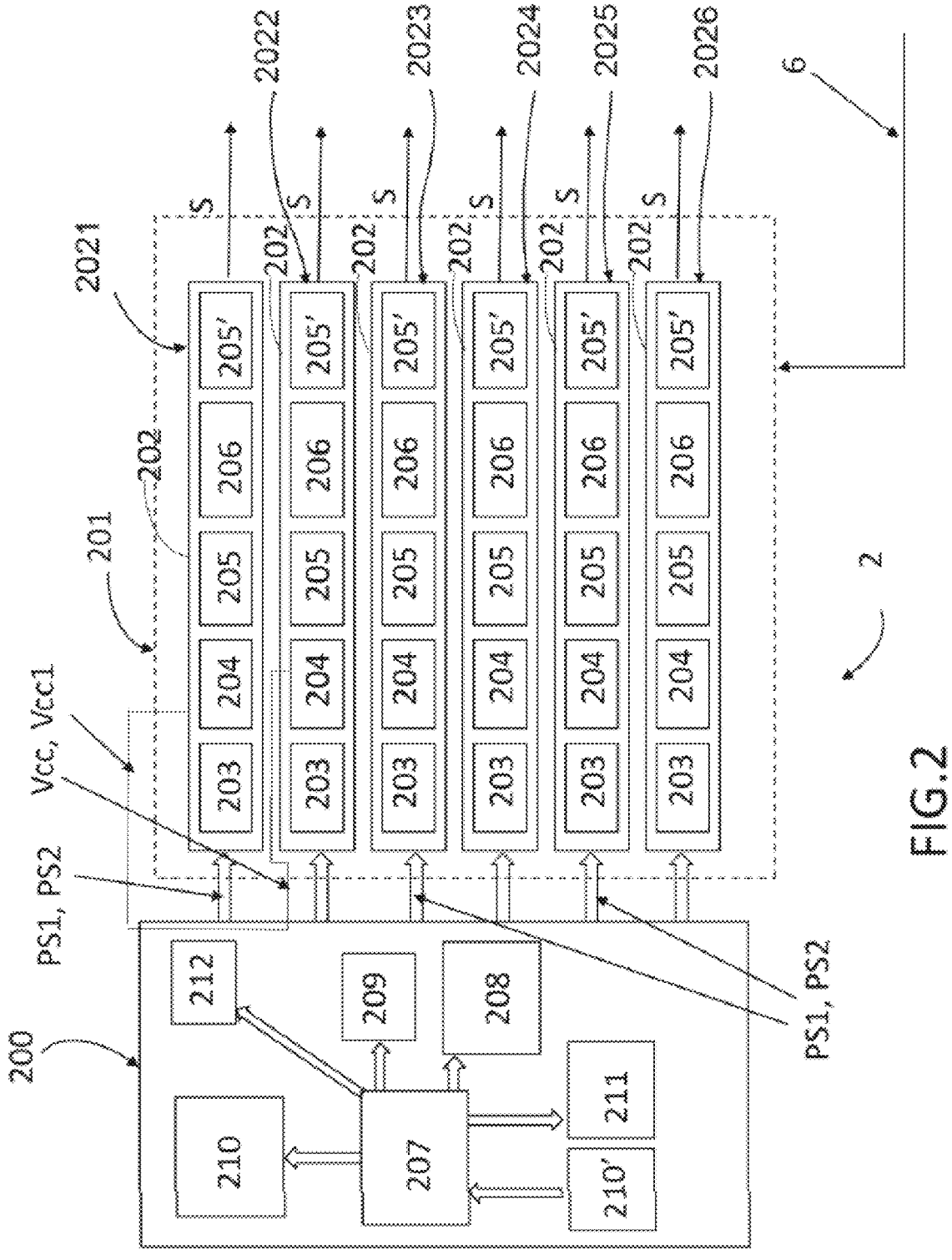
FIG. 2 shows, with a block diagram, the power generator of the electronic apparatus of FIG. 1 comprising a single control unit and a power unit.
Figure 12:
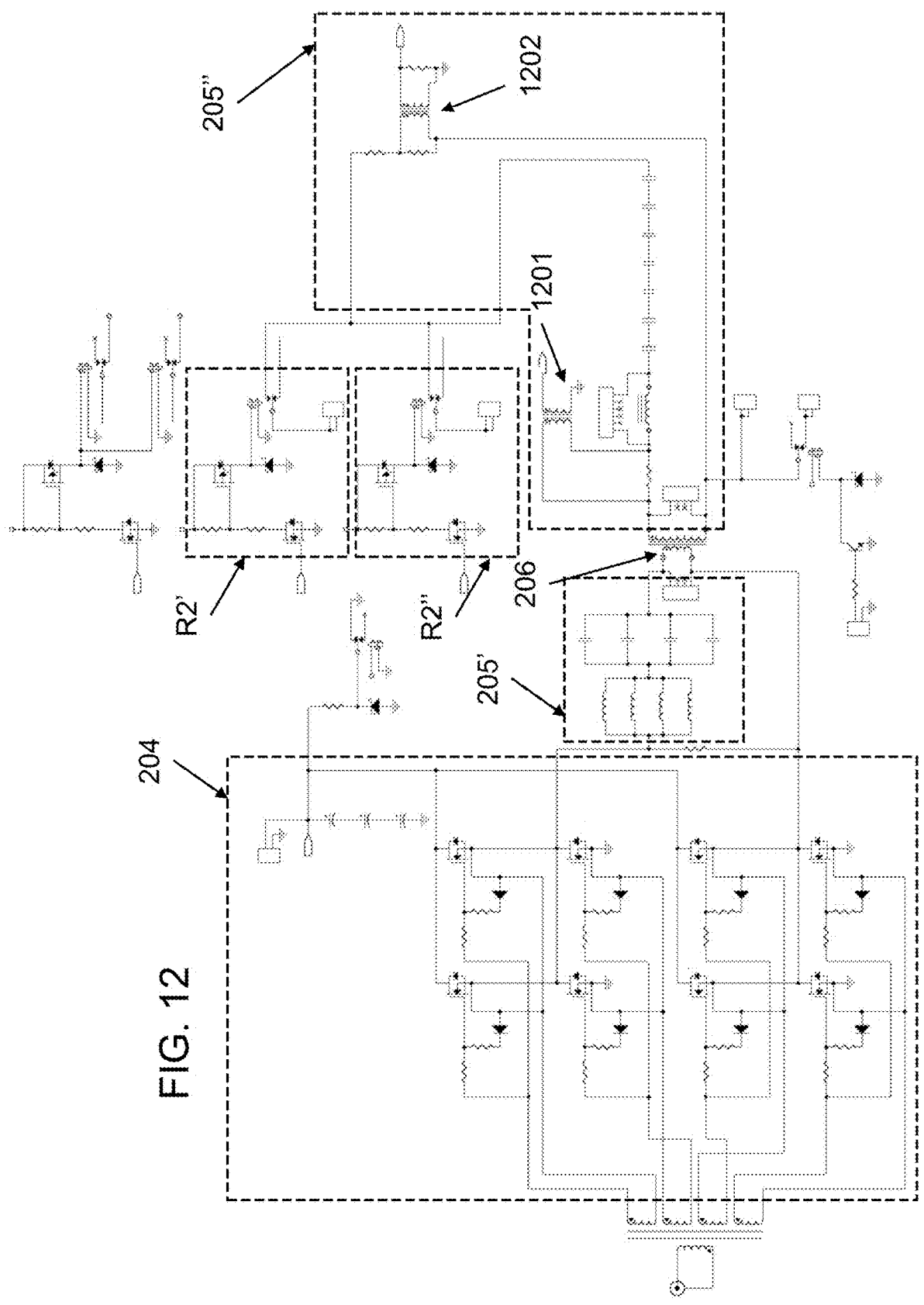

FIG. 12 illustrates an alternative example of the circuital structure of one of six power modules included in the power unit of the power generator of FIG. 2.

The same or similar elements are indicated in the drawings by the same reference numeral.

DESCRIPTION OF SOME PREFERRED EMBODIMENTS

The present invention can be understood more readily by reference to the following detailed description, examples, drawing, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention.

In accordance with a general embodiment, with reference to FIG. 1, an electronic apparatus for delivering Coherent Sine Burst Irreversible Electroporation energy, or IRE, to a biological tissue 1 to be treated according to the present invention is globally denoted by reference numeral 100.

The electronic apparatus 100 comprises a plurality of electrodes 3 positionable either on or near the biological tissue 1 to be treated and a power generator 2 for supplying electric energy to each of the electrodes 3 of said plurality. Particularly, the electrodes 3 of said plurality, six electrodes 3 are shown in the example of FIG. 1, are operatively associated to a catheter 4.

In a preferred embodiment, the biological tissue 1 to be treated is a cardiac tissue.

The power generator 2 is electrically connected to the electrodes 3, particularly with six wires 7, and is configured to generate an electric signal S to energize each of said electrodes 3, i.e. to apply voltage electric fields to the biological tissue 1 through the electrodes 3.

In addition, the electronic apparatus 100 comprises a further electrode 5 acting as a return electrode for the voltage electrical fields applied to the biological tissue 1. Particularly, this return electrode 5 or backplate is electrically connected to the power generator 2 through a respective return wire 6.

In an alternative embodiment (not shown in the figures) the electronic apparatus 100 can comprise a single electrode 3 positionable either on or near the biological tissue 1 to be treated. The power generator 2 is electrically connected to this single electrode 3 and is configured to generate an electric signal S to energize said electrode 3, i.e. to apply voltage electric fields to the biological tissue 1 through the single electrode 3.

Figure 3:
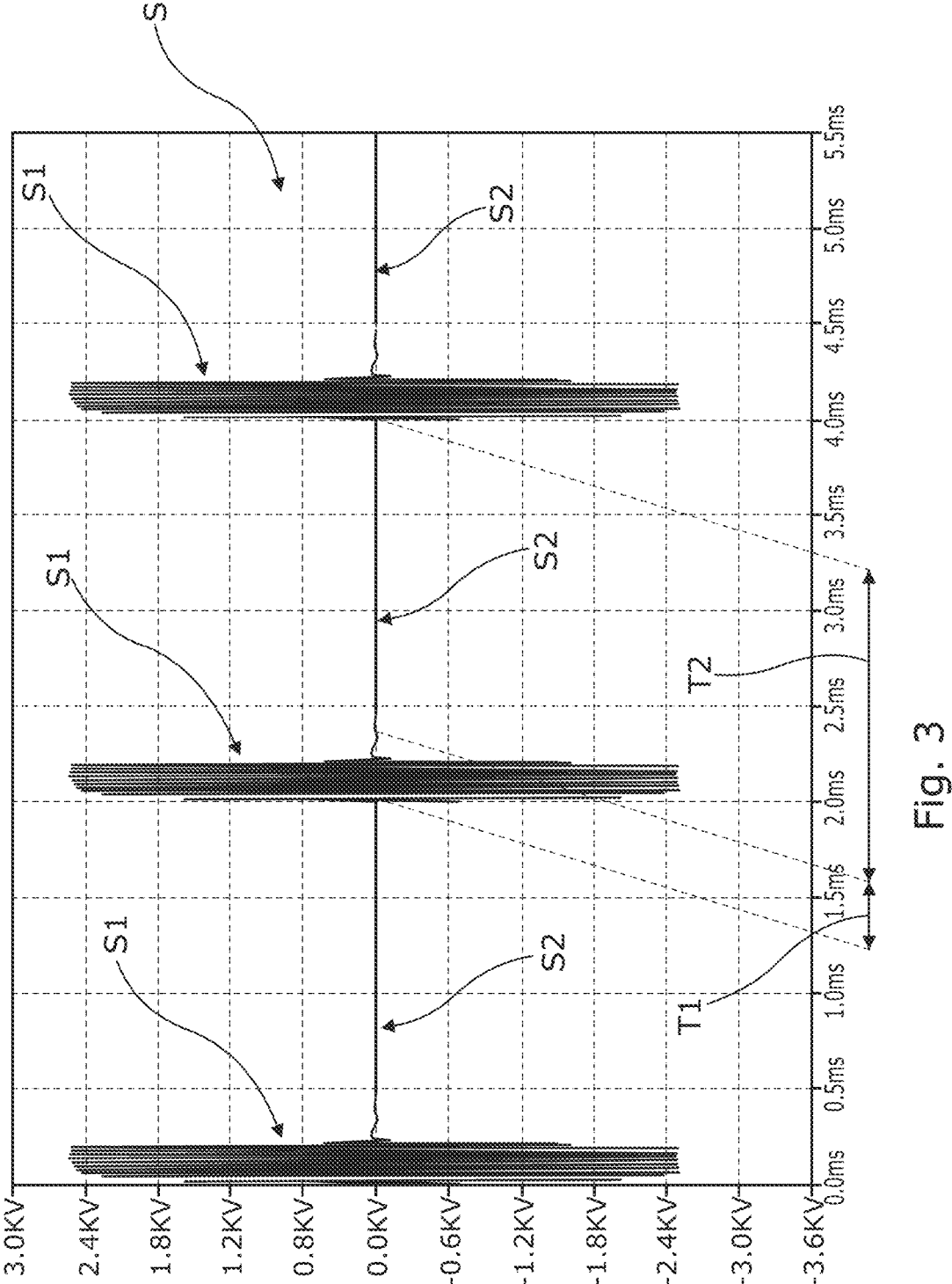
FIG. 3 shows, with a diagram as a function of time, an example of electric signal generated by the power generator of FIG. 1 by alternating over time a first electric signal with a second electric signal.
Figures 4, 5:
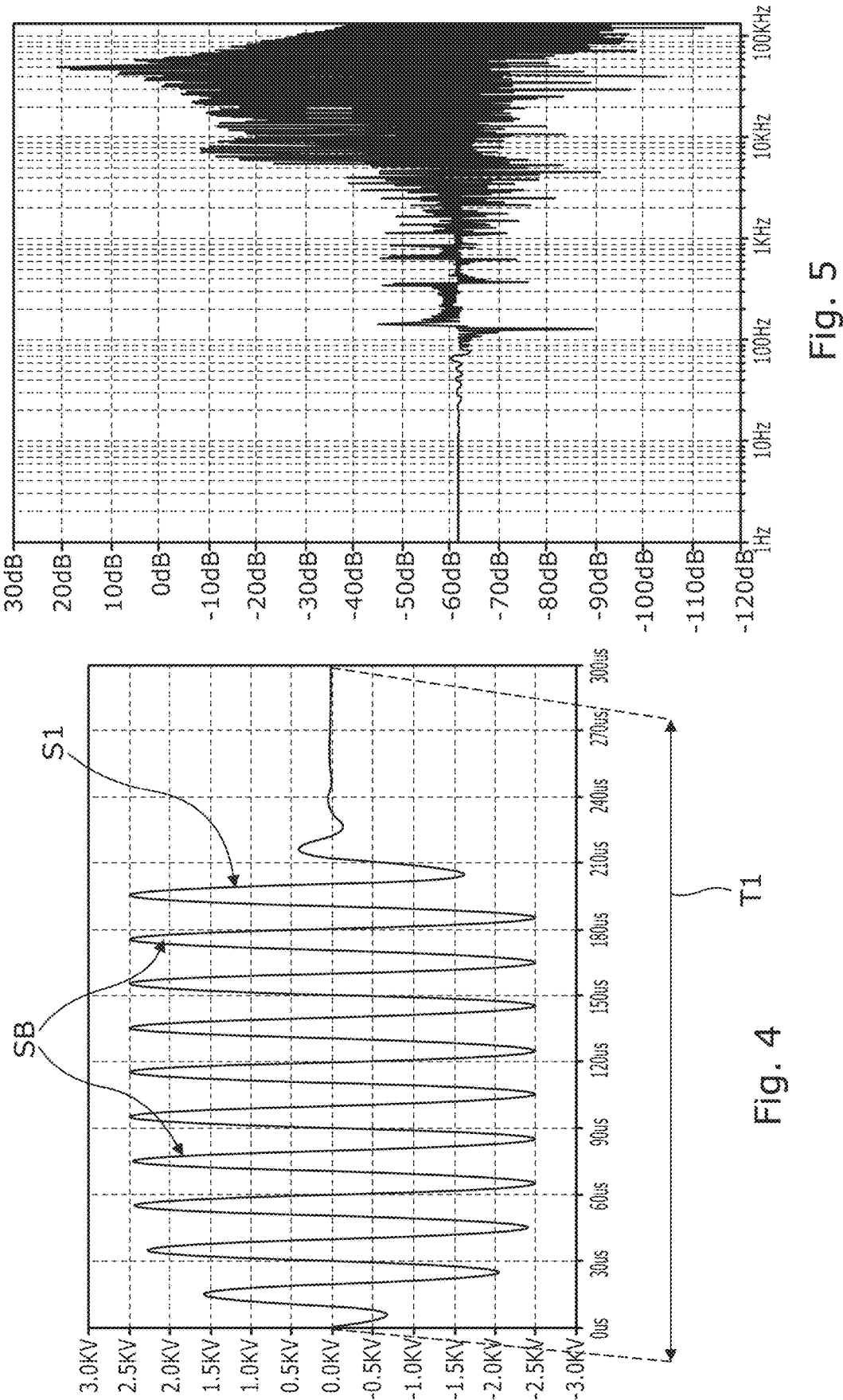
FIG. 4 shows at a higher resolution a portion of the diagram of FIG. 3 representing the first electric signal.
FIG. 5 illustrates a Fourier Analysis of the first electric signal including eleven basic sine waves at 50 KHz.

In more detail, with reference to FIGS. 3-4, the electric signal S is formed by alternating over time a first electric signal S1 with a second electric signal S2. The first electric signal S1 is supplied to the electrodes 3 during a first time interval T1 and the second electric signal S2 is supplied to the electrodes 3 during a second time interval T2 subsequent to the first time interval T1.

The first electric signal S1 is a continuous bipolar signal comprising two or more basic sine waves SB in said first time interval T1. Each basic sine wave consisting in one positive half-wave and one negative half-wave. The second electric signal S2 has an amplitude equal to zero in said second time interval T2.

For example, the electric signal S depicted in FIG. 3 comprises three electric signals S1, wherein two of said first electric signals S1 are spaced from one another by the second electric signal S2 which is null in the second time interval T2.

In an alternative embodiment, the first electric signal S1 comprises two or more basic sine waves SB repeated over said first time interval T1.

With the present invention, the Applicant proposes a power unit configured to generate an electric signal S for ablating the tissue 1 that consists of several sine wave bursts, i.e. a plurality of first electric signals S1, spaced by cooling periods, i.e. the second electric signals S2, in which no electrical energy is transferred to the electrodes 3. The sine wave bursts are created in a way that avoids stimulation of the heart, even if applied for longer periods of time. This is obtained by choosing the waveforms such that the net voltage of harmonic waves created in a region between 1 Hz and 200 Hz is negligible. In fact, the frequency interval 1 Hz and 200 Hz has to be avoided in order to avoid heart stimulation.

In more detail, the diagram of electric signal S shown in FIG. 3 includes three sine wave bursts, each spaced by a cooling period of 1.5 msec.

In FIG. 5, a Fourier Analysis diagram of the first electric signal S1 including eleven basic sine waves SB, for example at 50 KHz is depicted. Particularly, this Fourier Analysis diagram indicates that the voltage amplitude of the 50 kHz signal component, i.e. the desired component, is 67 dB higher than the 150 Hz signal component, which is the harmful component. In particular, a peak voltage of 1.5 kV for the signal component at 50 kHz corresponds about a peak voltage of 0.0005 V for the signal component at 150 Hz, i.e. a peak voltage near to zero which does not create heart stimulation.

In comparison, a traditional IRE square wave signal has a 150 Hz signal component at a voltage of around 6 V, which would create a significant risk of heart stimulation.

In accordance with an embodiment, the first electric signal S1 has a frequency in the range of 25-49 kHz. In accordance with an embodiment, the first electric signal S1 has a frequency in the range of 25-75 KHz.

In accordance with one or more embodiments, the first electric signal S1 has a frequency in the range of 35-65 kHz. In accordance with one or more embodiments, the first electric signal S1 has a frequency in the range of 40-60 kHz. In accordance with one or more embodiments, the first electric signal S1 has a frequency in the range of 45-55 kHz. In accordance with one or more preferable embodiments, the first electric signal S1 has a frequency of 50 KHz.

In accordance with an alternative embodiment, the first electric signal S1 comprises from two to fifteen basic sine waves SB in said first time interval T1.

In fact, depending on tissue ablation requirements, when a voltage applied to the tissue 1 with the electric signal S is selected to be higher, the generator 2 provides the first electric signal S1 including fewer basic sine waves SB repeated over the first time interval T1, i.e. fewer cycles of the first S1 and second S2 electric signals are required. On the contrary, when a voltage applied to the tissue 1 with the electric signal S is selected to be lower, the generator 2 provides the first electric signal S1 including more basic sine waves SB repeated over said first time interval, i.e. the more the number of cycles of the first S1 and second S2 electric signals are required. Therefore, the voltage applied to the tissue 1 with the electric signal S can be obtained as a trade off between the number of cycles and the number basic sine waves SB repeated over said first time interval T1.

In accordance with an alternative embodiment, the second time interval T2 of the second signal S2, i.e. the cooling period, has a duration from at least 1 milli-second to 1 second.

In particular, the duration of the second time interval T2 can be changed based on requirements for heat dissipations.

In accordance with an alternative embodiment, a peak-to-peak mean amplitude of each basic sine wave SB is in the range of 2.000 V to 20.000 V. The preferred amount is tissue dependent. In particular, upon power up of the power generator 2, the initial setting could be −2.5 kV and +2.5 kV before changing to accommodate the various tissue requirements.

In general, according to the some embodiments, properties of the electric signal S can be changed as long as the amplitude of signal components below a predetermined threshold are negligible. In general, according to some embodiments, properties of the electric signal S can be changed as long as the amplitude of signal components below 200 Hz are negligible.

In accordance with an alternative embodiment described with reference to FIGS. 1-2, the power generator 2 comprises a single control unit 200 and a power unit 201 for generating the electric signal S. Particularly, the power unit 201 is electrically connected to all electrodes 3 of said plurality of electrodes.

In accordance with an alternative embodiment, the power unit 201 is driven by the single control unit 200 to change the number of basic sine waves SB repeated over said first time interval T1 to modify the electric energy level associated to the signal S to be supplied to the electrodes 3.

In accordance with an alternative embodiment, the power unit 201 is driven by the single control unit 200 to change the duration of the second time interval T2 to modify the electric energy level associated to the signal S to be supplied to the electrodes.

In accordance with an alternative embodiment, the power unit 201 comprises a power module 202 driven by the single control unit 200 to generate said first electric signal S1 during the first time interval T1 and to generate said second electric signal S2 during the second time interval T2.

The power module 202 may comprise:

a selecting block 204 selectively controlled by a square wave signal, wherein the selecting block is configured to change the electric energy level associated with said electric signal S; and a filtering and electrical isolation block 205, 206, 205'.

Particularly, the power module 202 may comprise:

a drive circuit block 203 controlled by the single control unit 200 for generating said first S1 or second S2 electric signal starting from drive signals PS1, PS2 provided by the single control unit 200 or a signal null, respectively;

a selecting block 204 selectively controlled by said drive circuit block 203 to change continuously the electric energy level associated to said electric signal S;

a filtering and electrical isolation block 205, 206, 205'.

In accordance with an alternative embodiment, the single control unit 200 comprises one or more of a Microprocessor 207 configured to control a variable High Voltage Power Supply block 208 and a Programmable Logic Controller block 209. The variable High Voltage Power Supply block 208 is configured to provide a supply voltage signal Vcc, Vcc1 to the power module 202 for generating the electric signal S. In more detail, the supply voltage signal comprises a first direct current power supply voltage Vcc and a second direct current power supply voltage Vcc1. The first Vcc and second Vcc1 power supply voltage are in parallel with respective protection capacitors C10 and C2. In one or more embodiments, such as embodiments not including a drive circuit block 203, the voltage Vcc may not be necessary. Supply voltage Vcc may provide a voltage of 10-25 Volts, 15-20 Volts or preferably 18 Volts. Supply voltage Vcc1 may provide a voltage of 100-1000 Volts, 150-500 Volts, 175-300 Volts or, for example, 250 Volts. Supply voltage Vcc1 may be a variable supply voltage configured to vary between one or more of the above-listed ranges or another voltage range.

Figure 6:
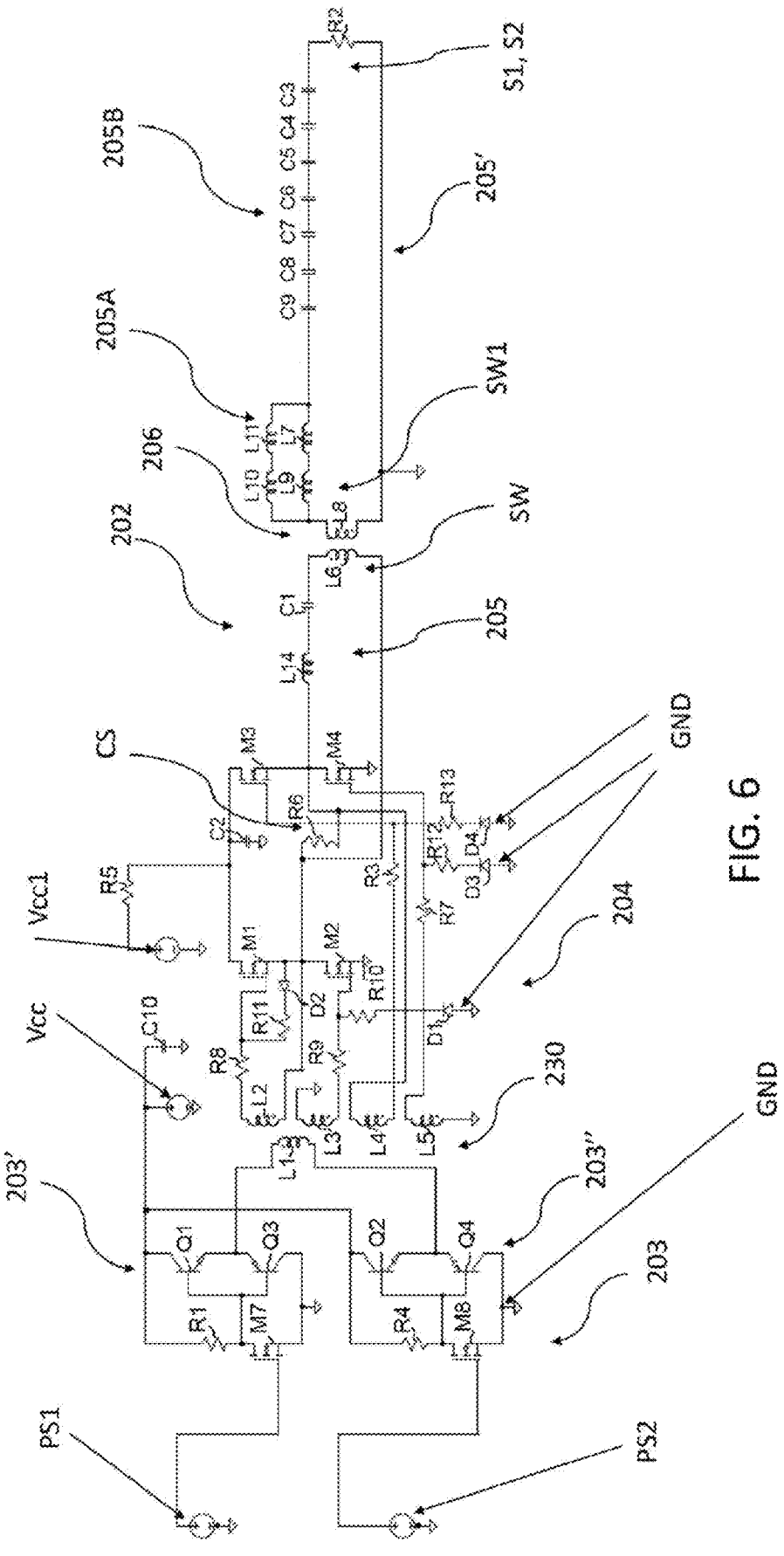
FIG. 6 illustrates an example of the circuital structure of one of six power modules included in the power unit of the power generator of FIG. 2.

FIG. 12 shows an example embodiment which does not utilize a drive block but does comprise a switching block and filtering and isolation block similar to those shown in FIG. 6.

The Programmable Logic Controller (PLC) block 209 is configured to generate said drive signals PS1, PS2 to control the drive circuit block 203 of the power module 202. A programmable logic controller may be particularly advantageous for generating signals PS1 and PS2, as these signals need to be provided at high frequencies, which the PLC may be particularly well suited to compared to alternative implementations for generating these signals.

In one or more alternative embodiments, a programmable logic controller block 209 may not be necessary and, instead PS1 and PS2 may be generated by a microprocessor device. In yet further alternative embodiments, a hard logic application-specific integrated circuit (ASIC) may be used to generate signals PS1 and PS2.

In some embodiments, a single drive signal PS may be used to provide a square wave drive signal, instead of providing two square wave signals. In such embodiments, the one might consider that a first drive signal is the same as a second drive signal. However, the practicalities in generating such a single drive signal using one of the above approaches or an alternative approach may be challenging. As such, the generation of first and second drive signals PS1 and PS2 may be particularly advantageous. In some embodiments, the second drive signal PS2 may be generated based on the first drive signal PS1 while in other embodiments the first and second drive signals PS1, PS2 may be generated independently.

In one or more embodiments, the one or both drive signals may be bipolar square wave signals or unipolar square wave signals. That is, the voltage levels of the one or both drive signals may be set at a relative zero volts and a relative positive voltage or the voltages levels may be set at a relative positive voltage and a relative negative voltage. It yet other examples, both voltages may be relatively positive compared to a reference voltage or relatively negative compared to a reference voltage. It will be appreciated that each of these may be equivalent and relative only to a voltage that is defined as zero volts for the purpose of the circuit.

Correspondingly, in one or more embodiments, the square wave input signal may be a bipolar square wave signal or a unipolar square wave signal. That is, the voltage levels of the square wave signal may be set at a relative zero volts and a relative positive voltage or the voltages levels may be set at a relative positive voltage and a relative negative voltage. It yet other examples, both voltages may be relatively positive compared to a reference voltage or relatively negative compared to a reference voltage. It will be appreciated that each of these may be equivalent and relative only to a voltage that is defined as zero volts for the purpose of the circuit.

The single control unit 200 further comprises on or more of:

a Video interface and Push Button block 210, 210' controlled by the Microprocessor 207 to set parameters of the electronic apparatus 100 and display the selected parameters;

a Watch Dog block 211 for controlling proper functioning of the Microprocessor 207;

an Audio interface block 212 for providing audio information representative of correctness of the electroporation process and/or errors occurred.

The control unit 200 may also include a visual feedback element, such as a light bar capable of emitting a number of different colours, which provides visible cues and/or information relating to the operating status or processing of the control unit, and/or any errors encountered by the control unit 200.

In accordance with an alternative embodiment, the power unit 201 comprises one or more power modules 202 equal to each other. In the example of FIG. 2, the power unit 201 comprises six power modules 202, however, other numbers of power modules 202 may be present, such as two, four or eight power modules 202. Each power module 202 is configured to generate and supply the electric signal S to one electrode 3.

In accordance with an embodiment, at least one of the electrodes 3 of said plurality of electrodes is a monopolar electrode, and said monopolar electrode is electrically connected to only one power module 202 of the power unit 201.

In a further embodiment, at least two of said electrodes 3 of said plurality of electrodes are electrically connected to form bipolar electrodes, and said bipolar electrodes are electrically connected separately to a respective power module 202 selectable among the power modules of said power unit 201.

In accordance with an embodiment, in order to provide either bipolar voltage or a combination of bipolar and unipolar voltage, the electric signals at the output of two or more power modules 202 of the power unit 201 have to be selected. For example, the power unit 201 may comprise two, four six or eight power modules 202 equal to each other. Particularly, with reference to FIG. 2, from top to bottom, a first power module 2021, a second power module 2022, a third power module 2023, a fourth power module 2024, a fifth power module 2025, a sixth power module 2026.

Single pairs can be formed by power modules 2021 and 2022 or power modules 2022 and 2023 or power modules 2023 and 2024 or power modules 2024 and 2025 or power modules 2025 and 2026.

The returns of all power modules 2021-2026 are connected together and correspond to the return wire 6.

For example, to provide either bipolar voltage or a combination of bipolar and unipolar voltage, the electric signals S generated by the first 2021, third 2023, fifth 2025 power modules are all at a same first phase value. The electric signals S generated by the second 2022, fourth 2024, sixth 2026 power modules are all at a second phase value, different from the first phase value.

According to an exemplary embodiment, when the difference between the first phase value and the second phase value is 60 degrees, the bipolar voltage generated by two adjacent power modules is the same as the unipolar voltage.

In accordance with an alternative embodiment, the power generator 2 is powered by a battery or is connected to a standard wall outlet of an AC electrical power grid capable of producing 110 volts or 240 volts.

In accordance with an alternative embodiment, each power module 202 may comprise a drive circuit block wherein each drive circuit block comprises an amplifier circuit. The amplifier circuit 203 may be arranged in an Emitter-Follower configuration.

In the case of an Emitter-Follower configuration, in order to generate the first electric signal S1 of said electric signal S, the amplifier circuit 203 is configured to amplify the drive signals generated by the single control unit 200. These drive signals comprise a first PS1 and a second PS2 pulsed signals supplied by the single control unit 200. In particular, the first pulsed signal PS1 comprises a first square wave, and the second PS2 pulsed signal comprises a second square wave wherein the second square wave is 180 degrees out of phase with respect to the first square wave. Further, the duty cycle, i.e. switching cycle, of the first pulsed signal PS1 and the second pulsed signal PS2 may be selected such that the primary winding L1 is not driven by the signals PS1 and PS2 simultaneously. In this way, conflict between the signals and potential resulting damage can be avoided. More particularly, the first pulsed signal PS1 may be on, i.e. provide a "logic high", for a first period, e.g. 10 μs, followed by both pulsed signals PS1, PS2 being 'off', i.e. providing a "logic null", e.g. for one clock cycle of approximately 62.5 ns, then the second pulsed signal PS2 being on, i.e. providing a "logic low", for a second period, e.g. 10 μs, followed by both pulsed signals PS1, PS2 being 'off' again, e.g. for one clock cycle of approximately 62.5 ns, before such a duty cycle repeats. The amplifier circuit 203 in this arrangement provides for level-shifting of the input signals PS1 and PS2 so that they are suitable for driving the H-Bridge circuit 204.

In order to generate the second electric signal S2 of said electric signal S, the single control unit 200 is configured to supply said amplifier circuit 203 with a respective drive signal null.

In other embodiments, the power module 202 may be configured to provide drive signals for provision to an H-Bridge circuit 204 without a drive circuit block. Instead, for example, the power module 202 may comprise circuitry and logic which is suitable to drive the H-bridge. Alternatively, there may be provided a drive circuit block which comprises a suitably-sized operational amplifier capable of providing a drive signal, thus negating the need for an Emitter-Follower arrangement and a transformer circuit. Advantages of such an implementation may be that lower voltages are handled by the H-bridge, and thus the electronic components therein need only have a lower voltage rating. However, a larger transformer 206 would be required later in the circuit in order to step up such low voltages to the high voltages needed for IReversible Electroporation. Such a larger transformer 206 later in the circuit would, in turn, require a greater current on its primary winding which would lead to complications instead with the current rating of the electronic components in the H-bridge.

As is described in further detail later, the drive circuit block, which may comprise the amplifier circuit arranged in an Emitter-Follower configuration, may be configured to drive an H-Bridge circuit of the selecting block via a first transformer circuit 230 which comprises a first primary winding L1 and four distinct secondary windings, L2-L5. In some embodiments, the primary and secondary windings may be arranged around a single common core such that they are electrically isolated but magnetically coupled. In other embodiments, a different arrangement may be implemented in order to provide the first transformer circuit 230. The secondary coils may comprise a first pair of secondary windings, such as secondary windings L2 and L5, an a second pair of secondary windings, such as secondary windings L3 and L4. The first pair of secondary windings are arranged such that they receive the signals PS1 and PS2 from the primary windings 180 degrees out of phase from the second pair of secondary windings. This is represented in FIG. 6 by a dot on the secondary windings and by whether the dotted or undotted side of said windings are coupled to the gate of their respect FET, M1-M4.

The use of a first transformer circuit 230 and the magnetic coupling it provides for between the amplifier circuit 203 and the H-Bridge may be particularly advantageous, as it provides for electrical isolation between these two portions of the circuit. This means that, if anything goes wrong on the amplifier circuit side of the first transformer circuit 230, the field effect transistors (FETs) of the H-bridge 204 will simply be open, as no signals will be provided to their gate terminals, and, consequently, the H-Bridge will have a null output signal. This provides a measure of protection not only to the electronic components of the H-Bridge 204 but also to the patient, as they are electrically isolated from the single control unit 200.

In accordance with an alternative embodiment, the selecting block 204 of each power module 202 comprises a H-Bridge circuit 204.

In order to generate the first electric signal S1 of said electric signal S, said H-Bridge circuit 204 is configured to combine the first PS1 and the second PS2 pulsed signals which, in some embodiments, are amplified by the amplifier circuit 203, to generate a combined signal CS having a square wave form.

In accordance with one or more embodiments, the filtering and electrical isolation block 205, 206, 205' of each power module 202 may comprises:

a first series resonance filter 205 configured to generate a sine wave signal SW by converting the square wave combined signal CS generated at the output of the H-Bridge circuit 204;

a transformer 206 configured to amplify said sine wave signal SW to generate a further sine wave signal SW1;

a second series resonance filter 205' configured to generate the first electric signal S1 of said electric signal S to be supplied to the electrodes 3 by filtering the further sine wave signal SW1.

Figures 7, 8:
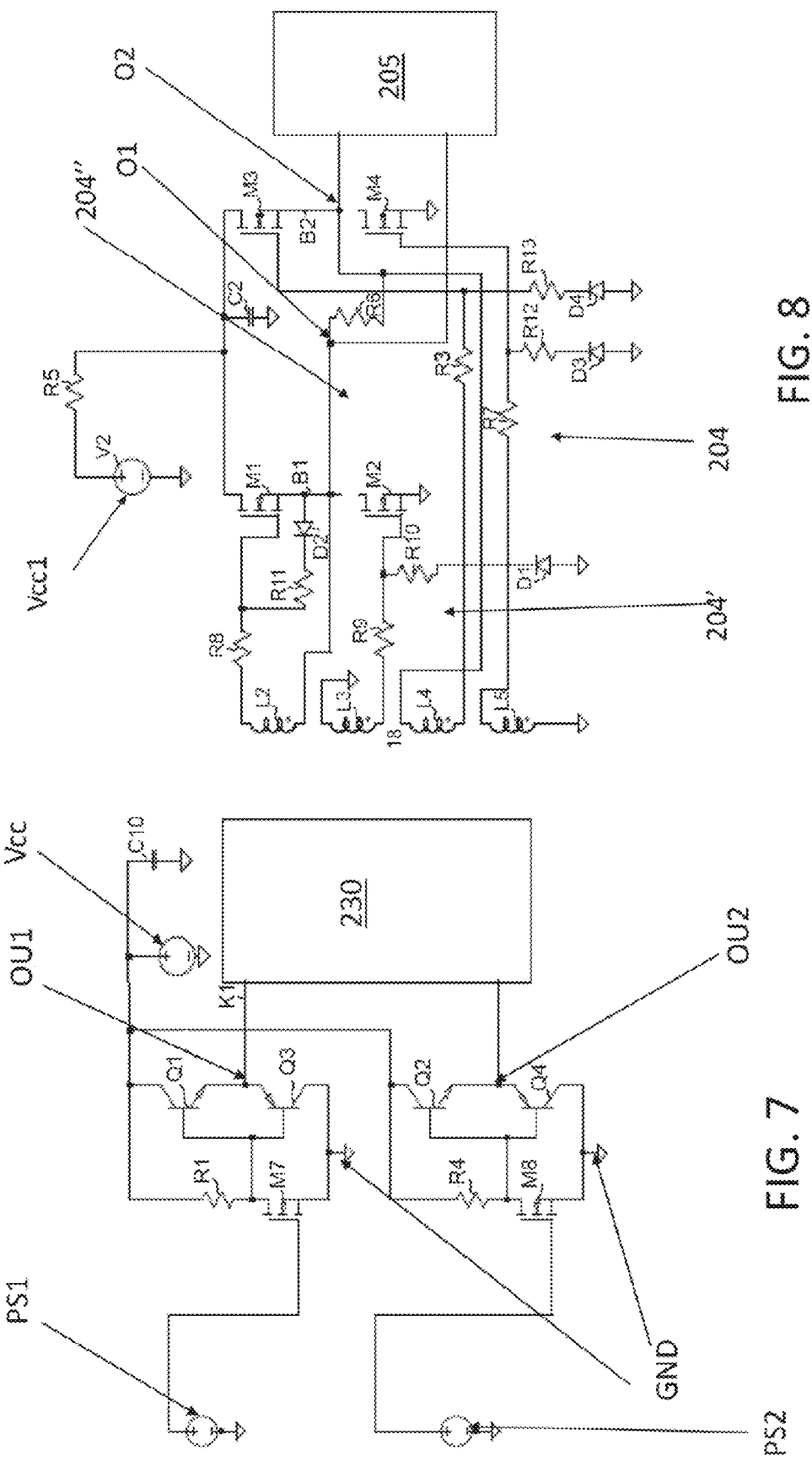
FIGS. 7, 8 and 9 show, with enlarged views, circuital portions of the power module circuital structure of FIG. 6.

With reference to FIGS. 6-7, a preferred embodiment of the amplifier circuit 203 in Emitter-Follower configuration is described in detail.

The amplifier circuit 203 comprises a first 203' and a second 203" amplifier circuit in Emitter-Follower configuration identical to each other. Each amplifier circuit 203', 203" is connected between the first direct current power supply voltage Vcc and a ground potential or ground GND terminal that is couplable to a ground potential. The ground potential may be a reference voltage such as a relative 0 Volt reference voltage. Any reference node or ground terminal referred to herein may comprise a ground node set to a relative 0 volts and any other ground terminal may be set to a same relative voltage, such as 0 volts, or to a different relative reference voltage appropriate for that portion of the circuit. It will further be appreciated that, typically, reference nodes, such as a ground node, are only considered coupled to ground when coupled to a power source. As such, reference to terminals being couplable to ground are understood by the skilled person as being a clear reference that a circuit does not need to be coupled to a power source to be an circuit according to the present disclosure but is configured to be so coupled in use.

The first amplifier circuit 203' comprises a first input circuit M7, R1, Q1, Q3 configured to receive as input the first PS1 pulsed signal. Particularly, the first input circuit comprises a first MOSFET transistor M7 configured to receive the first pulsed signal PS1 at a gate terminal and having a respective source terminal connected to ground GND. The first input circuit also comprises a first resistor R1 connected between the first power supply voltage Vcc and a drain terminal of the first MOSFET transistor M7. The drain terminal of the first MOSFET transistor M7 is electrically connected to respective base terminals of first BJT transistors, particularly two BJT transistors, Q1 and Q3 connected (with their respective collector terminals) between the first power supply voltage Vcc and the ground GND in an Emitter-Follower configuration. The emitter terminals of said first BJT transistors Q1 and Q3 are connected to a respective first output terminal OU1 of the first amplifier circuit 203'.

The second 203" amplifier circuit comprises a second input circuit M8, R4, Q2, Q4 configured to receive as input the second pulsed signal PS2. Particularly, the second input circuit comprises a second MOSFET transistor M8 configured to receive the second PS2 pulsed signal at a gate terminal and having a respective source terminal connected to ground GND. The second input circuit also comprises a second resistor R4 connected between the first power supply voltage Vcc and a drain terminal of the second MOSFET M8 transistor. The drain terminal of the second MOSFET transistor M8 is electrically connected to respective base terminals of second BJT transistors, particularly two second BJT transistors, Q2 and Q4 connected (with their respective collector terminals) between the first power supply voltage Vcc and the ground GND in an Emitter-Follower configuration. The emitter terminals of said second BJT transistors Q2 and Q4 are connected to a respective second output terminal OU2 of the second amplifier circuit 203".

The first and second pulsed signals PS1 and PS2 are provided to the amplifier circuits 203', 203" such that their respective logic high signals do not overlap. Signals are provided in this manner in order to avoid damaging components of the amplifier circuits 203', 203". The signals PS1 and PS2 may be configured to not overlap by way of appropriate selection of their frequencies and duty cycles.

The power module 202 comprises a first transformer circuit 230 interposed between the amplifier circuit or drive circuit block 203 and the H-Bridge circuit 204. In more detail, the transformer circuit 230 comprises an electrical transformer or isolator having a primary winding L1 and four secondary windings, particularly a first L2, second L3, third L4 and fourth L5 secondary windings. The primary windings to secondary windings may be provided at a ratio of 1:1 for the primary windings to each separate secondary windings.

Terminals of the primary winding L1 of the first transformer circuit 230 are connected to the output terminals OU1, OU2 of the first 203' and second 203" amplifier circuits, respectively. The H-Bridge circuit 204 comprises a power inverter block 204 configured to generate at its output the combined signal CS having a square wave form starting from the second direct current power supply voltage Vcc1 and by combining the first PS1 and the second PS2 pulsed signals amplified by the amplifier circuit 203.

In more detail, with reference to FIGS. 6 and 8, an example of the power inverter block 204 of the H-Bridge type included in the power module 202 of the invention is described below.

This power inverter block comprises a driving portion 204' of the H-Bridge inverter and a power portion 204" of the H-Bridge inverter.

In particular, the power portion 204" of the H-Bridge inverter 204 comprises:

a first inverter branch B1 comprising a first M1 and a second M2 power Mosfet (metal oxide semiconductor field effect transistor);

a second inverter branch B2 comprising a third M3 and a fourth M4 power Mosfet.

The MOSFETs may comprise silicon carbide field effect transistors or a different type of field effect transistor. A silicon carbide field effect transistor may be particularly suitable for use in the H-Bridge circuit 204, particularly where each silicon carbide field effect transistor is rated to operate continuously at 120 Amps. In some embodiments, the provision of two parallel transistors on each inverter branch may allow for the parallel transistor arrangement to sustain in excess of 200 Amps continuously.

The first M1 and third M3 power Mosfet are connected between a power supply terminal at the second power supply voltage in direct current Vcc1, through a resistor R5 of second direct current power supply voltage, and, respectively, a first O1 and a second O2 output terminals of the H-Bridge circuit 204.

The second M2 and fourth M4 power Mosfet are connected between the aforementioned first O1 and second O2 output terminals of the H-Bridge circuit 204 and the ground potential GND.

The power supply Vcc1 may be implemented as a supply voltage Vcc1 followed by a downstream resistor, such as resistor R5. Resistor R5 may be provided to limit the current delivered to capacitor C2 in order to prevent the circuit from drawing too much power from the charging power supply Vcc1. In one or more alternative embodiments, Vcc1 and resistor R5 may be replaced with a current source which is provided by a power source dedicated to the H-Bridge; this may be instead of from the variable high voltage power supply block 208. FIG. 12 shows an example wherein the charging capacitor C2 is provided as a bank of capacitors and the power supply Vcc1 is a current source with no need for an additional resistor.

The H-Bridge circuit comprises a power inverter 204 comprising a driving portion 204'. The driving portion 204' of the H-Bridge inverter 204 is described in detail below.

In particular, the gate terminal of the aforementioned first M1 power Mosfet is connected to one terminal of the first secondary winding L2 through a third resistor R8. The first O1 output terminal of the H-Bridge circuit 204 is connected to the gate terminal of the first power Mosfet M1 through a first diode D2 series connected to a fourth resistor R11. The other terminal of the first secondary winding L2 is directly connected to the first output terminal O1 of the H-Bridge circuit 204.

Furthermore, the gate terminal of the third M3 power Mosfet is connected to one terminal of the third secondary winding L4 through a fifth resistor R3. The gate terminal of the third Mosfet M3 is connected to ground GND through a sixth resistor R13 series connected to a second diode D4. The other terminal of the third secondary winding L4 is directly connected to the second output terminal O2 of the H-Bridge circuit 204.

In addition, the gate terminal of the second M2 power Mosfet is connected to one terminal of the second secondary winding L3 through a seventh resistor R9. The gate terminal of the second Mosfet M2 is connected to ground GND through a eighth resistor R10 series connected to a third diode D1. The other terminal of the second secondary winding L3 is directly connected to ground GND.

In addition, the gate terminal of the fourth M4 power Mosfet is connected to one terminal of the fourth secondary winding L5 through a ninth resistor R7. The gate terminal of the fourth Mosfet M4 is connected to ground GND through a tenth resistor R12 series connected to a fourth diode D3. The other terminal of the fourth secondary winding L5 is directly connected to ground GND.

It should be noted that the H-Bridge circuit 204 comprises the power inverter block 204 configured to generate the combined signal CS having a square wave form between the above mentioned first O1 and second O2 output terminals which are connected to each other with an output resistor R6.

In particular, the capacitor C2 is charged by the power supply Vcc1, which may or may not be a current source. Such charging may be provided continuously, but this need not necessarily be the case and is not in the example embodiment shown. In the example embodiment shown, upon receiving a logic-high signal from driver circuit 203', MOSFETs M1 and M4 turn on and thus connect the capacitor C2 across the output resistor R6 in a first direction. This discharges some current from the capacitor C2 and gives rise to a voltage across the output resistor R6 that is equal in magnitude to the voltage stored by the capacitor C2, i.e. Vcc1, and which is output by the H-bridge circuit 204 in the form of a first half, e.g. an upper or positive half, of a square wave of the combined signal CS. Meanwhile, when MOSFETs M2 and M3 receive a logic-high signal from the driver circuit 203' they turn on (with MOSFETs M1 and M4 being turned off by receipt of a logic-low signal from driver circuit 203') and thereby connect the capacitor C2 across the output resistor in a second direction, opposite the first direction. This again discharges some current from the capacitor C2 and gives rise a voltage across the output resistor R6 which is equal in magnitude to the remaining, slightly reduced, voltage stored by the capacitor C2, i.e. Vcc1'. This slightly reduced voltage is output by the H-bridge circuit 204 in the form of a second half, e.g. an upper or positive half, of the square wave of the combined signal CS. MOSFETs M1 and M4 are then again turned on, with MOSFETS M2 and M3 being turned off, and the selective switching of the capacitor C2 across the output resistor R6 in first and second directions continues, with the resulting voltage arising across the output resistor R6 being slightly reduced on each successive half square wave as the capacitor C2 discharges slightly more on each occasion. Accordingly, the H-bridge circuit 204 is controlled to output a combined signal CS having a square wave form with an amplitude which approximates to Vcc1×2.

Capacitor C2 may be appropriately sized such that each discharge instigated by a logic high PS1 or PS2 signal drains only a very small portion of the overall stored charge, i.e. stored voltage, such that the capacitor C2 is able to act as a reservoir of stored charge which helps to minimise the small reduction in voltage magnitude arising across the output resistor R6 during the output of successive half square waves, such that the combined signal CS output by the H-bridge circuit 204 continues to have a square wave form with an amplitude that closely approximates to Vcc1×2. By way of example, the capacitor may be a bank of capacitors having a total capacitance of 2,000 microFarads to 10,000 microFarads. In one or more examples, the H-bridge circuit 204 is required to switch pulses at a voltage of +20 V or −20 V. However, the first M1, second M2, third M3 and fourth M4 Mosfet transistors are only rated for a gate voltage of −7 V or more. Accordingly, the H-Bridge circuit 204 includes for each Mosfet transistor M1-M4 a respective diode, D1, D2, D3, D4 connected to a resistor R10, R11, R12, R13 for limiting the negative pulse to −7 V.

It will be appreciated that components M1-M4 do not need to be implemented as MOSFETs, however, components M1-M4 must be able to provide selective switching based on a received signal and must be able to manage the currents and voltages required for a power generator for supplying electric energy to a plurality of electrodes of an electronic apparatus for delivering Coherent Sine Burst Irreversible Electroporation energy. Components M1-M4 may, instead, be implemented as any power switching element. In one or more embodiments, a plurality of components may be provided in place of a single one of the components M1-M4. For example, two MOSFETs may be provided each with a gate terminal coupled a common secondary winding per component M1-M4, such as in the arrangement of FIG. 12. This may provide for a splitting of the load, and thereby the burden on a single power switching element.

After generating the combined signal CS having a square wave form at the H-bridge circuit 204, the power module 202 of the present invention comprises a first series resonance filter 205 for converting the combined signal CS into a sine wave signal SW.

With reference to FIG. 6, the first series resonance filter 205 is connected between the output of the H-bridge circuit 204 and the transformer 206 configured to amplify said sine wave signal SW to generate the further sine wave signal SW1. The transformer 206 comprises a first L6 winding and a second winding L8. Said further sine wave signal SW1 is provided between a respective first terminal of the second winding L8 of the transformer 206 and a respective second terminal connected to ground GND.

In accordance with an exemplary embodiment, the transformer 206 is a 1 to 3 ratio step up isolation transformer with a high frequency ferrite core. In yet other embodiments, the transformer 206 is a 1 to 4 ratio step up isolation transformer with a high frequency ferrite core. It will be appreciated that other step-up ratios may be used instead. In one or more embodiments, the high frequency ferrite core may be configured to operate in a frequency range of 40-60 KHz. In other embodiments, the high frequency ferrite core may be configured to operate in a frequency range of 35-65 KHz. In other embodiments, the high frequency ferrite core may be configured to operate in a frequency range of 45-55 KHz. In other embodiments, the high frequency ferrite core may be configured to operate at a frequency of 50 KHz.

In more detail, such first series resonance filter 205 may comprise an inductance L14 series connected with a capacitor C1. The so obtained sine wave signal is then amplified by the transformer L6/L8. The values of inductance L14 and capacitor C1 is determined by the specific application to IRE.

Alternatively, the first series resonance filter 205 may have an alternative arrangement. In one or more alternative embodiments, the first series resonance filter 205 may comprise a set of four inductors arranged in parallel such that an input of each inductor is coupled to the output of the H-Bridge circuit and the output of each of the four inductors are coupled together to provide a common inductor output, such as in the example shown in FIG. 12. The first series resonance filter 205 may further comprise a set of four capacitors arranged mutually in parallel such that the common output of the four parallel inductors is coupled to a common input of the four parallel capacitors and the four parallel capacitors are connected to a common capacitor output that is connected to an input of the transformer 206, such as in the example shown in FIG. 12. It will be appreciated that a different plurality of parallel inductors and parallel capacitors may be implemented in the first series resonance filter 205.

The first series resonance filter 205 is for example a band pass filter configured to filter all the harmonic components of the combined square wave signal CS except a base harmonic selected for the sine wave signal SW. For example, for a base harmonic of 40 kHz, typical values of inductance L14 and capacitor C1 are, for example: L14=10 pH, C1=1 μF.

Due to the high output voltage of the first sine wave electric signal S1 required for electroporation, the power module 202 of the present invention comprises also, advantageously, a second series resonance filter 205'.

This second series resonance filter 205' is required to have a significantly higher capacity than the series resonance filters known in the art, such as filters used for Radio Frequency Ablation or RFA.

This second series resonance filter 205' is neither required in RFA generators known in the art nor in square wave PFA generators.

According to an embodiment, this second series resonance filter 205' is connected between the transformer 206 and a load R2 of the power module 202. Particularly, the second series resonance filter 205' is connected between the first terminal of the second winding L8 of the transformer 206 and a load resistor R2. This load resistor R2 can be assimilated to the resistance associated to each electrode 3 of the electronic apparatus 100.

Preferably, the second series resonance filter 205' is a band pass filter configured to improve filtering of a base harmonic, for example of 40 kHz, selected for the further sine wave signal SW1.

In a preferred embodiment, the second series resonance filter 205' comprises an inductive circuital portion 205A series connected to a capacitive circuital portion 205B. Both the inductive circuital portion 205A the capacitive circuital portion 205B are connected between the first terminal of the second winding L8 of the transformer 206 and the load resistor R2.

In accordance with an exemplary embodiment, the inductive circuital portion 205A comprises four inductances, particularly a first L7, a second L9, a third L10 and a fourth L11 inductances. The first and second inductances L7-L9 are connected to each other in series, to form a first couple of inductances. The third and fourth inductances L10-L11 are connected to each other in series, to form a second couple of inductances. The two couples of inductances, L7-L9 and L10-L11 are connected to each other in parallel.

Typical values are L7=L9=L10=L11=760 μH.

In accordance with an alternative exemplary embodiment, the inductive circuital portion 205A may comprise an inductor choke such as a 750 micro Henry inductor choke configured to block signals at frequencies higher than the predetermined output frequency of signal S. It will be appreciated that alternative or additional inductive circuital portions may be used in the second series resonance filter.

In accordance with an exemplary embodiment, the capacitive circuital portion 205B of the second series of resonance filter 205' comprises a plurality of capacitors, particularly seven capacitors in the example shown in FIGS. 6 and 9, more particularly a first C3, a second C4, a third C5, a fourth C6, a fifth C7, a sixth C8 and a seventh C9 capacitors, that are connected to each other in series between the inductive circuital portion 205A and the load resistor R2. Providing for the capacitive circuital portion of the second series resonance filter 205' may be particularly advantageous for filtering out low-frequency signals which may otherwise cause undesirable stimulation of the heart.

Typical values are C3=C4=C5=C6=C7=C8=C9=1 μF.

One relevant advantage provided by embodiments comprising the amplifier circuit 203 in Emitter-Follower configuration is the low output impedance provided by this circuit. Particularly, this fact allows to maintain the output impedance of the H-Bridge circuit 204 of low values to avoid "ringing" due to the low pass filter associated to the first series resonance filter 205.

In fact, if the H-Bridge circuit 204 is not driven, using an amplifier 203 or in an alternative manner, none of the devices in the bridge conduct and a high impedance is provided to the transformer 206. This acts as a RF switch as a high impedance is seen looking back into the output of that power module 202. In this way, safety functionality is built-in to the present circuit such that safety is an inherent property of the circuit. This provides a contrast to solutions of the prior art which typically require additional components specifically dedicated to safety functionality.

Compared to the circuital solutions for power generators known in the art, for example the generators used in Radio-Frequency Ablation or RFA, the generators known in the art do not employ amplifier circuits in Emitter-Follower configuration, since in these circuits a sufficient amplification is already achieved at an output transformer.

In addition, square wave generators used for PFA do not require low output impedance as the square wave is never converted into sine waves and "ringing" due to low pass filters is not an issue.

FIG. 12 shows an alternative example of the circuital structure of one of six power modules included in the power unit of the power generator of FIG. 2. Like components have been correspondingly labelled in FIG. 12, where appropriate. It can be seen that this figure provides examples of embodiments different from that of FIG. 6. For example, the embodiment of FIG. 12 does not comprise a driver block comprising one or more amplifier circuits and, instead, receives a bipolar input signal at a primary winding of a transformer. The H-Bridge 204 of FIG. 12 utilises two power switching elements per power switching element employed in the embodiment of FIG. 6. This embodiment is described earlier in the specification.

An alternative first series resonant filter 205' is shown comprising four parallel inductors in series with four parallel capacitors.

An alternative second series resonant filter 205" is shown comprising an inductor choke in place of the inductor circuital portion of FIG. 6. This example second series resonant filter 205" further comprises a current measurement circuit 1201 and a voltage measurement circuit 1202. Providing one or both of a current measurement circuit 1201 and a voltage measurement circuit 1202 may be particularly advantageous, as they may allow one to take a direct measurement of the current, voltage and/or power of the signal S applied to a patient via the one or more electrodes. This may be particularly in contrast to solutions which do not make use of the same isolation functionality provided by the embodiments herein. Providing for more accurate measurements of one or all of current, voltage and power may be particularly advantageous for safety monitoring of a patient and for allowing for improved control of signals applied to a patient via the one or more electrodes.

Finally, the embodiment of FIG. 12 explicitly shows example loads R2' and R2" representative of the circuits for providing the signal S to the electrodes.

The present application also discloses a method for controlling the plurality of electrodes in the electronic apparatus 100 for delivering Coherent Sine Burst Irreversible Electroporation energy, wherein the apparatus comprises a plurality of electrodes 3 and a power generator 2.

The method comprising the step of generating by the power generator 2 an electric signal S for supplying electric energy to each of the electrodes 3 of said plurality. The electric signal S is formed by alternating over time a first electric signal S1 with a second electric signal S2. The first electric signal S1 is a continuous bipolar signal comprising two or more basic sine waves SB in a first time interval T1, each basic sine wave consisting in one positive half-wave and one negative half-wave. The second electric signal S2 has an amplitude equal to zero in a second time interval T2 subsequent to the first time interval T1.

The method further comprising the steps of:

supplying said first electric signal S1 to the electrodes 3 of said plurality during the first time interval T1;

supplying said second electric signal S2 to the electrodes 3 of said plurality during the second time interval T2.

In accordance with an alternative embodiment, the power generator 2 comprises a single control unit 200 and a power unit 201 electrically connected to all electrodes 3 of said plurality of electrodes. The method further comprising the step of driving, by the single control unit 200, the power unit 201:

to change the number of basic sine waves SB repeated over said first time interval T1, or to change the duration of the second time interval T2 to modify the electric energy level associated to the signal S to be supplied to the electrodes 3.

In accordance with an alternative embodiment, said step of driving comprises:

in order to generate the first electric signal S1 of said electric signal S, amplifying a first PS1 and a second PS2 pulsed signals supplied by the single control unit 200 to the power unit 201, said first pulsed signal PS1 comprising a first square wave, and said second PS2 pulsed signal comprising a second square wave, said second square wave being 180 degrees out of phase with respect to the first square wave;

in order to generate the second electric signal S2 of said electric signal S, supplying, by the single control unit 200, the power unit 201 with the signal null.

In accordance with an alternative embodiment, in order to generate the first electric signal S1 of said electric signal S, the method further comprising: combining the first PS1 and the second PS2 pulsed signals to generate a combined signal CS having a square wave form;

generating a sine wave signal SW by converting the square wave combined signal CS;

amplifying said sine wave signal SW to generate a further sine wave signal SW1;

filtering the further sine wave signal SW1 to generate the first electric signal S1 to be supplied to the electrodes 3. In accordance with an alternative embodiment, a method is provided for controlling a single electrode 3 in an electronic apparatus 100 for delivering Coherent Sine Burst Irreversible Electroporation energy wherein the apparatus comprises a single electrode and a power generator 2 according to the present invention.

With reference to FIGS. 10A and 10B, alternative embodiments of the electronic apparatus 100 for delivering Coherent Sine Burst Irreversible Electroporation energy, or IRE, to a biological tissue 1 according to the present invention can be described.

Particularly, the electronic apparatus 100 comprises a first 30 and a second 31 electrodes positionable either on or near the biological tissue 1 to be treated, and the power generator 2. As indicated in FIG. 10A, the power generator 2 is configured to supply both electrodes 30, 31, respectively, with two sine-waves electrical signals Va and Vb "in phase", particularly voltage signals. As indicated in FIG. 10B, the power generator 2 is configured to supply both electrodes 30, 31, respectively, with two sine-wave electrical signals Va and Vb "out of phase", particularly with a phase difference of 180 degrees.

In more detail, with reference to FIG. 10A, the power generator 2 is configured to deliver unipolar power for Irreversible Electroporation to the tissue 1 driven by the difference in voltage between the first 30 and second 31 electrodes and the ground potential (0 V) associated to the return electrode 5.

In this case, current flows from the first 30 and second 31 electrodes to ground, i.e. to the return electrode 5. There is no voltage difference between the first 30 and second 31 electrodes at any moment in time—thus no bipolar current flow.

As the voltage oscillates between positive and negative peaks, the current moves to and from the ablation and return electrode 5.

With reference to FIG. 10B, the power generator 2 of the invention is configured to deliver simultaneously both unipolar and bipolar power for Irreversible Electroporation to the tissue 1. In this case, voltage is applied both between each of the first 30 and the second 31 electrodes and the ground potential (0 V) associated to the return electrode 5 and through the same electrodes 30, 31 to each other.

These features of the electronic apparatus 100 of the invention can be described particularly with reference to FIG. 11 showing schematically a plurality of electrodes 3 electrically supplied by the power generator 2 (not shown) of the invention. These electrodes 3 are operatively associated to a catheter 4 positionable either on or near a myocardial tissue 1 to be treated.

In an embodiment, the power generator 2 of the invention is configured to deliver to the electrodes 3 combined bi-polar and uni-polar voltages. A unipolar voltage is the voltage Va or Vb applied from each electrode 3 and the return electrode 5. Bipolar voltage, particularly voltage Va-Vb, is applied between two adjacent electrodes 3.

In a different embodiment, the power generator 2 of the invention is configured to alternate uni-polar and bi-polar voltage fields, for example by time division multiplexing.

For example, the power generator 2 of the invention uses 3500 Volts delivered to each electrode 3 during the first time interval T1 of the electric signal S above mentioned.

During the off-period of the electric signal S, i.e. during the second time interval T2, the output of each power module 202 is disconnected from the corresponding electrode 3.

In more detail, the power generator 2 of the invention can operate to deliver IRE energy according to a sequence of three types of voltage delivery that repeats.

In case of unipolar voltage only: voltage is applied from each electrode 3 to patient return electrode 5; this first step is followed by an off-period.

In case of unipolar and bipolar voltage combined: in a first step voltage is applied from each electrode 3 to patient return electrode 5; this first step is followed by a second step in which voltage is applied across two adjacent electrodes; both steps are followed by an off period.

According to an embodiment, by choosing the different combined, the ratio between bipolar and unipolar can be varied from 4 to 1 to all uni-polar.

By switching off the connection to the return electrode 5 in the electronic apparatus 100, and setting the phase shift of voltages Va and Vb to 180 degrees an all bi-polar mode can be produced.

According to alternative embodiments, an object of the present invention is to provide an electronic apparatus 100 for delivering Irreversible Electroporation energy, or IRE, to a biological tissue 1 to be treated. The electronic apparatus comprises one or more electrodes 3 positionable either on or near the biological tissue 1 to be treated and a power generator 2 for supplying electric energy to said one or more electrodes 3; said power generator 2 is configured to generate an electric signal S to energize said one or more electrodes 3.

The electric signal S is formed by alternating over time a first electric signal S1 with a second electric signal S2; said first electric signal S1 is supplied to the one or more electrodes 3 during a first time interval T1 and said second electric signal S2 is supplied to the one or more electrodes during a second time interval T2 subsequent to the first time interval T1; said first electric signal S1 has a periodic waveform in the first time interval T1; said second electric signal S2 has an amplitude equal to zero in the second time interval T2.

According to an embodiment, the periodic waveform of the first electric signal S1 has a frequency in the range of 25-49 kHz.

According to an alternative embodiment, the periodic waveform of the first electric signal S1 has a frequency in the range of 40-60 KHz.

According to a further embodiment, the second time interval T2 of the second signal S2 has a duration from at least 1 milli-second to 1 second.

According to alternative embodiments, a method for the ablation of a biological tissue 1 is provided. The method involves the step of using the electronic apparatus 100 for delivering Coherent Sine Burst Irreversible Electroporation energy, or IRE, according to the invention.

According to an alternative embodiment, said biological tissue 1 to be ablated is selected from the group comprising: cardiac tissue, renal nerve, splenic nerve, tumors, cancer cells.

According to an alternative embodiment, said electronic apparatus 100 for delivering Coherent Sine Burst Irreversible Electroporation energy, or IRE, comprises a plurality of electrodes 3 positionable either on or near the biological tissue 1 to be ablated, and a power generator 2 configured to generate an electric signal S to energize each of said electrodes 3. Said electric signal S is formed by alternating over time a first electric signal S1 with a second electric signal S2; the first electric signal S1 is supplied to the electrodes 3 during a first time interval T1 and the second electric signal S2 is supplied to the electrodes during a second time interval T2 subsequent to the first time interval T1; the first electric signal S1 is a continuous bipolar signal comprising two or more basic sine waves SB in said first time interval T1, each basic sine wave consisting in one positive half-wave and one negative half-wave; the second electric signal S2 has an amplitude equal to zero in said second time interval T2, thereby causing the ablation of said biological tissue 1.

According to an alternative embodiment, the first electric signal S1 has a frequency in the range of 25-49 kHz or in the range of 40-60 KHz.

According to alternative embodiments, a method for the treatment of a pathology in a patient is provided. The method involves the step of performing the ablation of a biological tissue 1 of said patient by using the electronic apparatus 100 for delivering Coherent Sine Burst Irreversible Electroporation energy, or IRE, according to the invention.

According to an alternative embodiment, said pathology in a patient is selected from the group comprising: hypertension, heart failure, tumour.

According to an alternative embodiment, said biological tissue 1 is selected from the group comprising: cardiac tissue, renal nerve, splenic nerve, tumors, cancer cells.

According to alternative embodiments, a method for the ablation of a biological tissue 1 by delivering Irreversible Electroporation energy, or IRE, is provided. The method involves the step of applying to said biological tissue 1 an electric signal S comprising at least a sine wave signal.

According to a preferred embodiment, said electric signal S is formed by alternating over time a first electric signal S1 with a second electric signal S2; said first electric signal S1 is applied during a first time interval T1 and said second electric signal S2 is applied during a second time interval T2 subsequent to the first time interval T1; the first electric signal S1 is a continuous bipolar signal comprising two or more basic sine waves SB in said first time interval T1, each basic sine wave consisting in one positive half-wave and one negative half-wave; the second electric signal S2 having an amplitude equal to zero in said second time interval T2, thereby causing the ablation of said biological tissue 1.

According to a further preferred embodiment, said first electric signal S1 has a frequency in the range of 25-49 kHz or in the range of 40-60 KHz.

According to an alternative embodiment, said biological tissue 1 is selected from the group comprising: cardiac tissue, renal nerve, splenic nerve, tumors, cancer cells.

According to alternative embodiments, a method for the treatment of a pathology in a patient by delivering Irreversible Electroporation energy, or IRE, is provided. The method comprises the step of applying to a biological tissue 1 of said patient an electric signal S formed by alternating over time a first electric signal S1 with a second electric signal S2; said first electric signal S1 is applied during a first time interval T1 and said second electric signal S2 is applied during a second time interval T2 subsequent to the first time interval T1; the first electric signal S1 is a continuous bipolar signal comprising two or more basic sine waves SB in said first time interval T1, each basic sine wave consisting in one positive half-wave and one negative half-wave; the second electric signal S2 has an amplitude equal to zero in said second time interval T2, thereby causing the ablation of said biological tissue 1.

According to a preferred embodiment, the first electric signal S1 has a frequency in the range of 25-49 kHz or in the range of 40-60 KHz.

According to an alternative embodiment, said pathology in a patient is selected from the group comprising: hypertension, heart failure, tumour.

The electronic apparatus 100 of present invention provides further relevant advantages.

In particular, the power generator 2 configured to generate a first electric signal S1 including basic sinusoidal waves SB rely on transformers, particularly transformer 206 and first transformer circuit 230. Therefore, a high level of electrical isolation is ensured for the patient.

Furthermore, the electronic apparatus of the invention 100 ensures a high degree of flexibility for energy delivery by modifying the number of basic sine waves SB of the first electric signal S1, the peak-to-peak amplitude of these sinewaves and the duration of the second time interval T2. Therefore, lengths and depths of lesions caused by the IRE procedure can be tailored.

Electrodes delivering a sinusoidal-wave can be on, off or anything on the scale of zero degrees to 360 degrees out of phase.

In addition, the Applicant has verified that the cost of components to design and manufacture the power generator 2 for generating a sinusoidal-wave is significant less than the cost for manufacturing generators of a square-wave known in the art.

LIST OF REFERENCE NUMERALS

100 Electronic apparatus
1 biological tissue
2 power generator
3 electrodes
30 first electrode
31 second electrode
4 catheter
5 further electrode, return electrode
6 return wire
7 wire
S electric signal
S1 first electric signal
S2 second electric signal
T1 first time interval
T2 second time interval
SB basic sine wave
200 single control unit
201 power unit
202 power module
203 drive circuit block—amplifier circuit in emitter Follower configuration
204 selecting block—H-Bridge circuit—power inverter block
205 first series resonance filter
206 electrical isolation block-transformer
205' second series resonance filter
207 Microprocessor
208 variable High Voltage Power Supply block
209 Programmable Logic Controller block
210 Video interface block
210' Push Button block
211 Watch Dog block
212 Audio interface block
230 first transformer circuit
Vcc supply voltage signal—first direct current power supply voltage
Vcc1 supply voltage signal—second direct current power supply voltage
GND ground potential
PS1 first pulsed signal
PS2 second pulsed signal
CS combined signal
SW sine wave signal
SW1 further sine wave signal
203' first amplifier circuit
203" second amplifier circuit
M7 first MOSFET transistor
R1 first resistor
Q1, Q3 first BJT transistors
Q2, Q4 second BJT transistors
M8 second MOSFET transistor
R4 second resistor
OU1 first output terminal of the first amplifier circuit 203'
OU2 second output terminal of the second amplifier circuit 203"
207 first transformer circuit L1 primary winding
L2 first secondary winding
L3 second secondary winding
L4 third secondary winding
L5 fourth secondary winding
204' driving portion of the H-Bridge inverter
204" power portion of the H-Bridge inverter
B1 first inverter branch
B2 second inverter branch
M1 first power Mosfet
M2 second power Mosfet
M3 third power Mosfet
M4 fourth power Mosfet
R5 resistor of second direct current power supply voltage
O1 first output terminal
O2 second output terminal
R8 third resistor
D2 first diode
R11 fourth resistor
R3 fifth resistor
R13 sixth resistor
D4 second diode
R9 seventh resistor
R10 eighth resistor
D1 third diode
R7 ninth resistor
R12 tenth resistor
D3 fourth diode
R6 output resistor
L6 first winding of transformer 206
L8 second winding of transformer 206
L14 inductance
C1 capacitor
R2 load resistor
205A inductive circuital portion
205B capacitive circuital portion
L7 first inductance
L9 second inductance
L10 third inductance
L11 fourth inductance
C3 first capacitor
C4 second capacitor
C5 third capacitor
C6 fourth capacitor
C7 fifth capacitor
C8 sixth capacitor
C9 seventh capacitor
C2, C10 protection capacitors
Va, Vb sine-wave electrical signals
2021 first power module
2022 second power module
2023 third power module
2024 fourth power module
2025 fifth power module
2026 sixth power module.

The invention claimed is:

1. A power unit for supplying electric energy to at least one electrode of an electronic apparatus for delivering Coherent Sine Burst Irreversible Electroporation energy, the power unit including at least one power module configured to generate an electric signal (S) to energize one or more respective electrodes, each power module comprising:
a selecting block configured to receive at least one square wave input signal, wherein the selecting block is configured to continuously change an electric energy level associated with said electric signal (S) based on the at least one square wave input signal in order to provide a combined signal at an output of the selecting block, and wherein the combined signal comprises a square wave waveform; and
a filtering and electrical isolation block configured to convert the combined signal into a sine wave signal and to filter the sine wave signal to generate the electric signal (S), wherein the conversion and filtering are electrically isolated from one another;
wherein the selecting block comprises an H-Bridge circuit and a charging capacitor, the charging capacitor having a first node coupled between a power supply terminal that is couplable to a second power supply voltage source and a ground terminal that is couplable to ground, the charging capacitor is configured to be selectively discharged via the H-Bridge circuit based on the at least one square wave input signal, and the selective discharging of the charging capacitor is configured to provide the combined signal at the output of the selecting block.

2. The power unit of claim 1, wherein the H-Bridge Circuit comprises:
a first inverter branch comprising a first power switching element and a second power switching element;
a second inverter branch comprising a third power switching element and a fourth power switching element;
said first power switching element and third power switching element are connected between the power supply terminal couplable to the second power supply voltage and, respectively, a first output terminal and a second output terminal of the H-Bridge circuit;
said second power switching element and fourth power switching element are connected between said first output terminal and second output terminal of the H-Bridge circuit and a ground terminal couplable to ground.

3. The power unit of claim 2, wherein gate terminals of each of the first power switching element, the second power switching element, the third power switching element and the fourth power switching element are controlled in response to the at least one square wave input signal in order to provide for the continuous change in electric energy level associated with the electric signal (S).

4. The power unit of claim 1, wherein the filtering and electrical isolation block comprises at least one of:
a first series resonance filter configured to generate the sine wave signal by converting the square wave combined signal at the output of the selecting block;
a step-up transformer configured to provide for the electrical isolation by being configured to amplify said sine wave signal to generate a further sine wave signal; and
a second series resonance filter configured to provide for filtering of the further sine wave in order to generate the electric signal to be supplied to the electrodes.

5. The power unit of claim 4, wherein the first series resonance filter comprises a bandpass filter configured to convert the combined signal into the sine wave signal at a predetermined frequency.

6. The power unit of claim 4, wherein the step-up transformer comprises a step-up transformer with a high frequency ferrite core.

7. The power unit of claim 4, wherein the second series resonance filter comprises one or both of:
an inductor choke, wherein the inductor choke is configured to provide for filtering of frequencies higher than the predetermined frequency; and at least one filter capacitor, wherein the filter capacitor is configured to provide for filtering of frequencies lower than the predetermined frequency.

8. The power unit of claim 1, wherein the filtering and isolation block further comprises one or both of:

a current measurement circuit configured to measure a current of the electric signal (S); and a voltage measurement circuit configured to measure a voltage of the electric signal (S).

9. The power unit of claim 1, further comprising a drive circuit configured to receive a first drive signal (PS1) and a second drive signal (PS2) wherein the drive circuit is configured to amplify the first and second drive signals in order to provide a first square wave input signal and a second square wave input signal to the selecting block.

10. The power unit of claim 9, further comprising a transformer circuit interposed between the drive circuit and the selecting block, wherein the transformer circuit is configured to provide for electrical isolation between the drive circuit and the selecting block.

11. The power unit of claim 10, wherein the transformer circuit comprises a primary winding having a first terminal coupled to a first output terminal of the drive circuit and a second terminal coupled to a second output terminal of the drive circuit and the transformer further comprising a first secondary winding, a second secondary winding, a third secondary winding, and a fourth secondary winding.

12. The power unit of claim 11, wherein the first drive signal and the second drive signal are different signals and the first drive signal and the second drive signal are provided to the drive circuit such that the first square wave input signal and the second square wave input signal are not provided to the transformer circuit contemporaneously.

13. The power unit of claim 11, wherein each of the first secondary winding, the second secondary winding, the third secondary winding and the fourth secondary winding are coupled to a respective one of the first power switching element, second power switching element, third power switching element and fourth power switching element of the H-Bridge circuit such that the first and second square wave input signals provide for control of the first, second, third, and fourth power switching elements.

14. A power unit for supplying electric energy to an electrode of an electronic apparatus, the power unit including a power module configured to generate an electric signal to energize the electrode, the power module comprising:

a selecting block configured to receive at least one square wave input signal and continuously change an electric energy level associated with said electric signal based on the at least one square wave input signal to provide a combined signal at an output of the selecting block, the combined signal comprising a square wave waveform; and a filtering and electrical isolation block configured to convert the combined signal into a sine wave signal and filter the sine wave signal to generate the electric signal, wherein the conversion and filtering are electrically isolated from one another, and the filtering and electrical isolation block comprises at least one of a current measurement circuit configured to measure a current of the electric signal and a voltage measurement circuit configured to measure a voltage of the electric signal.

15. The power unit of claim 14, wherein the selecting block comprises an H-Bridge circuit and a charging capacitor that has a node coupled between a power supply terminal and a ground terminal; and wherein the power supply terminal is couplable to a second power supply voltage source and the ground terminal is couplable to ground.

16. The power unit of claim 15, wherein the charging capacitor is configured to be selectively discharged via the H-Bridge circuit based on the at least one square wave input signal to output the combined signal from the selecting block.

17. A power unit for supplying electric energy to an electrode of an electronic apparatus, the power unit including a power module configured to generate an electric signal to energize the electrodes, the power module comprising:

a selecting block configured to receive a square wave input signal and continuously change an electric energy level associated with said electric signal based on the square wave input signal to output a combined signal that comprises a square wave waveform;

a filtering and electrical isolation block configured to convert the combined signal into a sine wave signal that is filtered to generate the electric signal, wherein the conversion and filtering are electrically isolated from one another; and a drive circuit configured to receive and amplify a first drive signal (PS1) and a second drive signal (PS2) to provide a first square wave input signal and a second square wave input signal to the selecting block.

18. The power unit of claim 17, further comprising:

a transformer circuit interposed between the drive circuit and the selecting block, wherein the transformer circuit is configured to electrically isolate the drive circuit and the selecting block.

19. The power unit of claim 17, wherein the filtering and electrical isolation block comprises a step-up transformer configured to electrically isolate the drive circuit and the selecting block by amplifying said sine wave signal to generate a second sine wave signal.

20. The power unit of claim 17, wherein the filtering and electrical isolation block comprises:

a first series resonance filter configured to generate the sine wave signal by converting the square wave combined signal; and a second series resonance filter configured to filter the second sine wave signal to generate the electric signal supplied to the electrode.

\* \* \* \* \*